(12) United States Patent
Wang et al.

(10) Patent No.: US 8,077,936 B2
(45) Date of Patent: Dec. 13, 2011

(54) TREATMENT PLANNING SOFTWARE AND CORRESPONDING USER INTERFACE

(75) Inventors: Hongwu Wang, Milpitas, CA (US); John R. Dooley, Castro Valley, CA (US); Bai Wang, Palo Alto, CA (US); Jay B. West, Mountain View, CA (US); I-Ning Chang, Fremont, CA (US); Neda Sayan, Los Altos, CA (US)

(73) Assignee: Accuray Incorporated, Sunnyvale, CA (US)

( * ) Notice: Subject to any disclaimer, the term of this patent is extended or adjusted under 35 U.S.C. 154(b) by 1147 days.

(21) Appl. No.: 11/242,366

(22) Filed: Sep. 30, 2005

(65) Prior Publication Data

US 2006/0274885 A1 Dec. 7, 2006

Related U.S. Application Data

(63) Continuation-in-part of application No. 11/145,121, filed on Jun. 2, 2005.

(60) Provisional application No. 60/692,606, filed on Jun. 20, 2005.

(51) Int. Cl.
*G06K 9/00* (2006.01)

(52) U.S. Cl. ...................................................... 382/128

(58) Field of Classification Search .................... 382/128
See application file for complete search history.

(56) References Cited

U.S. PATENT DOCUMENTS

| | | | |
|---|---|---|---|
| 5,341,292 A * | 8/1994 | Zamenhof | 600/425 |
| 6,038,283 A | 3/2000 | Carol et al. | |
| 6,238,342 B1 | 5/2001 | Feleppa et al. | |
| 6,393,096 B1 | 5/2002 | Carol et al. | |
| 6,556,199 B1 | 4/2003 | Fang et al. | |
| 6,757,423 B1 | 6/2004 | Amini | |
| 7,158,661 B2 | 1/2007 | Inoue | |
| 7,362,848 B2 | 4/2008 | Saracen et al. | |
| 7,831,289 B2 * | 11/2010 | Riker et al. | 600/407 |
| 2002/0102023 A1 | 8/2002 | Yamauchi | |
| 2003/0053669 A1 | 3/2003 | Suri et al. | |
| 2003/0065260 A1 * | 4/2003 | Cheng et al. | 600/427 |
| 2003/0072411 A1 * | 4/2003 | Welsh | 378/65 |
| 2003/0099397 A1 | 5/2003 | Matsugu et al. | |
| 2005/0201516 A1 | 9/2005 | Ruchala et al. | |
| 2005/0262467 A1 | 11/2005 | Croffie | |
| 2006/0072802 A1 | 4/2006 | Higgs et al. | |
| 2006/0274925 A1 | 12/2006 | West et al. | |
| 2006/0293583 A1 | 12/2006 | Saracen et al. | |
| 2007/0053490 A1 | 3/2007 | Wang et al. | |
| 2007/0127623 A1 * | 6/2007 | Goldman et al. | 378/65 |

OTHER PUBLICATIONS

Leksell, L., "The stereotactic method and radiosurgery of the brain", Acta Chirurgica Scandanavica 102 (1951), pp. 316-319.

Holder, A., "A tutorial on radiation oncology and optimization", In Greenberg, H.J., ed.: Tutorials on Emerging Methodologies and Applications in Operations Research. Kluwer Academic Press (2004).

Ferris, M., Lim, J., Shepard, D.: "An optimization approach for the radiosurgery treatment planning", SIAM Journal on Optimization 13 (2003), pp. 921-937.

Cheek, S., Holder, A., Fuss, M. Salter, B.: "The relationship between the number of shots and the quality of Gamma Knife Radiosurgeries." Technical Report 84, Department of Mathematics, Trinity University, San Antonio, TX (2004).

(Continued)

*Primary Examiner* — John Strege

(74) *Attorney, Agent, or Firm* — Lowenstein Sandler PC

(57) ABSTRACT

A method and apparatus for treatment planning are described.

23 Claims, 18 Drawing Sheets

OTHER PUBLICATIONS

Rosen, I., Lane, R., Morrill, S., Belli, J.: "Treatment plan optimization using linear programming", Medical Physics 18 (1991), pp. 141-152.

Shepard, D., Ferris, M., Olivera, G., Mackie, T.: "Optimizing the delivery of radiation therapy to cancer patients", SIAM Review 41 (1999) pp. 721-744.

Bartolozzi, F., De Gaetano, A., DiLena, E., Marino, S., Nieddu, L., Patrizi, G.: "Operational research techniques in medical treatment and diagnosis: a review." European Journal of Operations Research 121 (2000) pp. 435-466.

Holder, A.: "Radiotherapy treatment design and linear programming". Technical Report 70, Department of Mathematics, Trinity University, San Antonio, TX (2002).

Dantzig, G.B., Orden, A., Wolfe, P.: "The generalized Simplex method for minimizing a linear form under linear inequality restraints". Pacific Journal of Mathematics 5 (1955), pp. 183-195.

Paddick, I.: "A simple scoring ratio to index the conformality of radiosurgical treatment plans", Journal of Neurosurgery 93 (2000), pp. 219-222.

D. Bechmann, N. Dubreuil, "Animation through space and time based on a space deformation model", The Journal of Visualization and Computer Animation, 4(3) 165-184, 1993.

M. Levoy, et al., "Volume Rendering in Radiation Treatment Planning", Proc. First Conference on Visualization in Biomedical Computing, IEEE Computer Society Press, Atlanta, Georgia, May 1990, pp. 4-10.

Jay B. West et al., "Hybrid point-and-intensity-based deformable registration for abdominal CT images", Medical Imaging 2005, pp. 204-211.

Levoy, M., Fuchs, H., Pizer, S.M., Rosenman, J., Chaney, E.L., Sherouse, G.W., Interrante, V., Kiel, J., "Volume Rendering in Radiation Treatment Planning", Proc. First Conference on Visualization in Biomedical Computing, IEEE Computer Society Press, Atlanta, Georgia, May 1990, pp. 4-10.

Rudiger Westermann, Thomas Ertl, "Efficiently Using Graphics Hardware in Volume Rendering Applications", © 2000/2001 ACM. Reprinted with permission, from Proc. ACM SIGGRAPH 1998, pp. 169-178.

Klaus Engel, Martin Kraus, Thomas Ertl, "High-Quality Pre-Integrated Volume Rendering Using Hardware-Accelerated Pixel Shading", © 2001 ACM. Reprinted, with permission, from ACM SIGGRAPH/Eurographics Workshop on Graphics Hardware 2001, pp. 9-16, 121.

Jurgen Hesser et al., "Three Architectures for Volume Rendering", Eurographics '95, vol. 14, No. 3, 1995.

John Dooley, "Cyberknife® SRS System On-Target™ Treat Planning System, Clinical User's Guide", Accuray Incorporated, P/N 017790, Rev. F, 2005.

DeWyngaert, J.K., Noz, M.E., Ellerin, B., Kramer, E.L., Maguire, G.Q., Zeleznik, M.P., "Procedure for unmasking localization information from ProstaScint scans for prostate radiation therapy treatment planning", International Journal of Radiation Oncology, Biology, Physics, vol. 60, No. 2, pp. 654-662, 2004, Published by Elsevier.

U.S. Appl. No. 11/145,121, Office Action dated Oct. 31, 2008, 30 pages.

IEEE Transaction on Medical Imaging, vol. 17, No. 1, Feb. 1998, Automatic Detection of the Boundary of the Calcaneus from Ultrasound Parametric Images Using an Active Contour Model; Clinical Assessment; Francoise Lefebvre, Genevieve Berger, and Pascal Laugier, IEEE 0278-0062/98, 1998.

IEEE Transaction on Medical Imaging, vol. 16, No. 6, Dec. 1997, Method for Segmenting Chest CT Image Data Using an Anatomical Model: Preliminary Results; Matthew S. Brown, Michael F. McNitt-Gray, Nicholas J. Mankovich, Jonathan G. Goldin, John Hiller, Laurence S. Wilson, and Denise R. Aberle, IEEE 0278-0062/97, 1997.

U.S. Appl. No. 11/220,838, Notice of Allowance dated Apr. 14, 2010, 24 pages.

U.S. Appl. No. 11/220,838, Final Office Action dated Dec. 14, 2009, 14 pages.

U.S. Appl. No. 11/220,838, Office Action dated Jan. 23, 2009, 16 pages.

U.S. Appl. No. 11/220,838, Restriction Requirement dated Oct. 28, 2008, 7 pages.

U.S. Appl. No. 11/220,838, Notice of Allowance dated Jun. 22, 2010, 15 pages.

* cited by examiner

Register User Interface 700

TREATMENT PLANNING SOFTWARE AND CORRESPONDING USER INTERFACE

This application is a continuation-in-part of application Ser. No. 11/145,121, filed Jun. 2, 2005, which is hereby incorporated by reference, and claims the benefit of U.S. Provisional Application No. 60/692,606, filed Jun. 20, 2005, the contents of which are incorporated by reference herein.

TECHNICAL FIELD

The present invention relates generally to radiation treatment and, more particularly, to treatment planning.

BACKGROUND

Tumors and lesions are types of pathological anatomies characterized by abnormal growth of tissue resulting from the uncontrolled, progressive multiplication of cells, while serving no physiological function.

Pathological anatomies can be treated with an invasive procedure, such as surgery, but can be harmful and full of risks for the patient. A non-invasive method to treat a pathological anatomy (e.g., tumor, legion, vascular malformation, nerve disorder, etc.) is external beam radiation therapy. In one type of external beam radiation therapy, an external radiation source is used to direct a sequence of x-ray beams at a tumor site from multiple angles, with the patient positioned so the tumor is at the center of rotation (isocenter) of the beam. As the angle of the radiation source changes, every beam passes through the tumor site, but passes through a different area of healthy tissue on its way to the tumor. As a result, the cumulative radiation dose at the tumor is high and the average radiation dose to healthy tissue is low.

The term "radiotherapy" refers to a procedure in which radiation is applied to a target region for therapeutic, rather than necrotic, purposes. The amount of radiation utilized in radiotherapy treatment sessions is typically about an order of magnitude smaller, as compared to the amount used in a radiosurgery session. Radiotherapy is typically characterized by a low dose per treatment (e.g., 100-200 centiGray (cGy)), short treatment times (e.g., 10 to 30 minutes per treatment) and hyperfractionation (e.g., 30 to 45 days of treatment). For convenience, the term "radiation treatment" is used herein to mean radiosurgery and/or radiotherapy unless otherwise noted by the magnitude of the radiation.

Conventional isocentric radiosurgery systems (e.g., the Gamma Knife) use forward treatment planning. In forward treatment planning, a medical physicist determines the radiation dose to be applied to a tumor and then calculates how much radiation will be absorbed by critical structures (i.e., vital organs) and other healthy tissue. There is no independent control of the two dose levels for a given number of beams, because the volumetric energy density at any given distance from the isocenter is a constant, no matter where the isocenter is located.

In inverse planning, in contrast to forward planning, the medical physicist specifies the minimum dose to the tumor and the maximum dose to other healthy tissues independently, and the treatment planning software then selects the direction, distance, and total number and energy of the beams in order to achieve the specified dose conditions. One conventional treatment planning system that utilizes inverse planning is the On-Target™ Treatment Planning System produced by Accuray, Inc. of California. Conventional treatment planning software packages, such as the aforementioned, are designed to import 3-D images from a diagnostic imaging source, for example, magnetic resonance imaging (MRI), positron emission tomography (PET) scans, angiograms and computerized x-ray tomography (CT) scans. These anatomical imaging modalities such as CT are able to provide an accurate three-dimensional model of a volume of interest (e.g., skull or other tumor bearing portion of the body) generated from a collection of CT slices and, thereby, the volume requiring treatment can be visualized in three dimensions.

During inverse planning, a volume of interest (VOI) is used to delineate structures to be targeted or avoided with respect to the administered radiation dose. That is, the radiation source is positioned in a sequence calculated to localize the radiation dose into a VOI that as closely as possible conforms to the tumor requiring treatment, while avoiding exposure of nearby healthy tissue. Once the target (e.g., tumor) VOI has been defined, and the critical and soft tissue volumes have been specified, the responsible radiation oncologist or medical physicist specifies the minimum radiation dose to the target VOI and the maximum dose to normal and critical healthy tissue. The software then produces the inverse treatment plan, relying on the positional capabilities of the radiation treatment system, to meet the min/max dose constraints of the treatment plan.

FIG. 1 is a conceptual illustration of a graphical output of a treatment planning system displaying a slice of a CT image. The illustration of the CT image includes a pathological anatomy that is targeted for treatment, and well as a critical region that is positioned near the pathological anatomy. The treatment planning software enables the generation of a critical region contour around the critical region and a target region contour around the pathological anatomy. Conventionally, a user manually delineates points (e.g., some of the dots on the contour lines of FIG. 1) on the display that is used by the treatment planning software to generate the corresponding contours. While this may seem an easy task, such matching is difficult due to the three-dimensional nature and irregularities of the pathological and normal anatomies. Based on specified minimum dose to the target region and the maximum dose to the critical region, the treatment planning software generates the dose isocontour for the target region. The dose isocontour represents a given dose percentage (e.g., 60%, 70%, 80%, etc.) of a specified prescription dose for the target region. Ideally, the dose isocontour should perfectly match the contour of the target region. In some cases, the dose isocontour generated by the treatment planning software is not optimal, and can include portions of the critical region, as illustrated in FIG. 1.

The two principal requirements for an effective radiation treatment system are homogeneity and conformality. Homogeneity is the uniformity of the radiation dose over the volume of the target (e.g., pathological anatomy such as a tumor, lesion, vascular malformation, etc.) characterized by a dose volume histogram (DVH). An ideal DVH for the pathological anatomy would be a rectangular function as illustrated in FIG. 2, where the dose is 100 percent of the prescribed dose over the volume of the pathological anatomy and zero elsewhere. A desirable DVH for a critical region would have the profile illustrated in FIG. 3, where the volume of the critical anatomical structures receives as little of the prescribed dose as possible.

Conformality is the degree to which the radiation dose matches (conforms to) the shape and extent of the target (e.g., tumor) in order to avoid damage to critical adjacent structures. More specifically, conformality is a measure of the amount of prescription (Rx) dose (amount of dose applied) within a target VOI. Conformality may be measured using a conformality index (CI)=total volume at>=Rx dose/target volume at>=Rx dose. Perfect conformality results in a CI=1. With conventional radiotherapy treatment, using treatment planning software, a clinician identifies a dose isocontour for a corresponding VOI for application of a treatment dose (e.g., 3000 cGy).

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The present invention is illustrated by way of example, and not by way of limitation, in the figures of the accompanying drawings.

DETAILED DESCRIPTION

Figure 1:
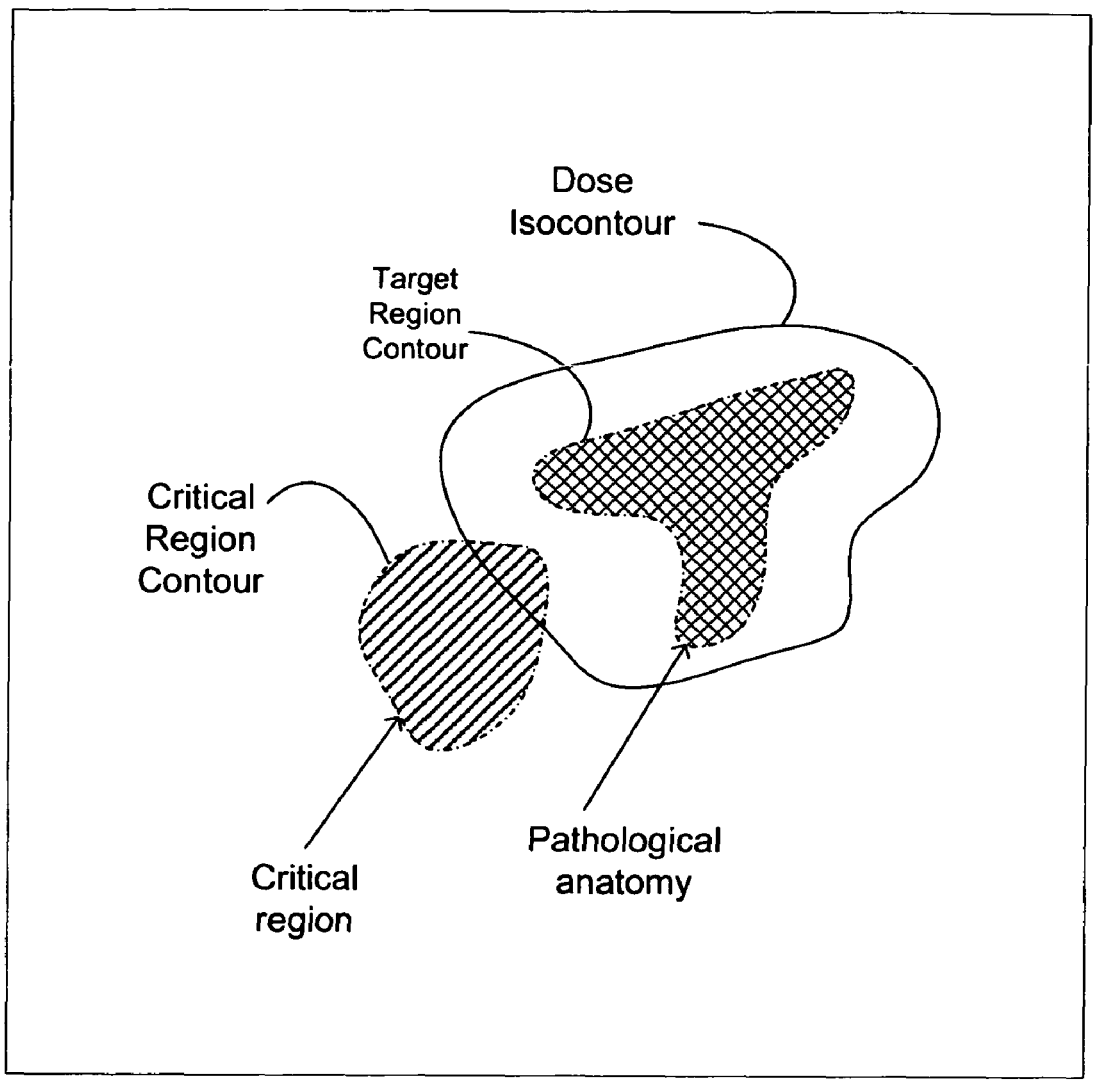
FIG. 1 illustrates a graphical output of a treatment planning software displaying a slice of a CT image.
Figure 2:
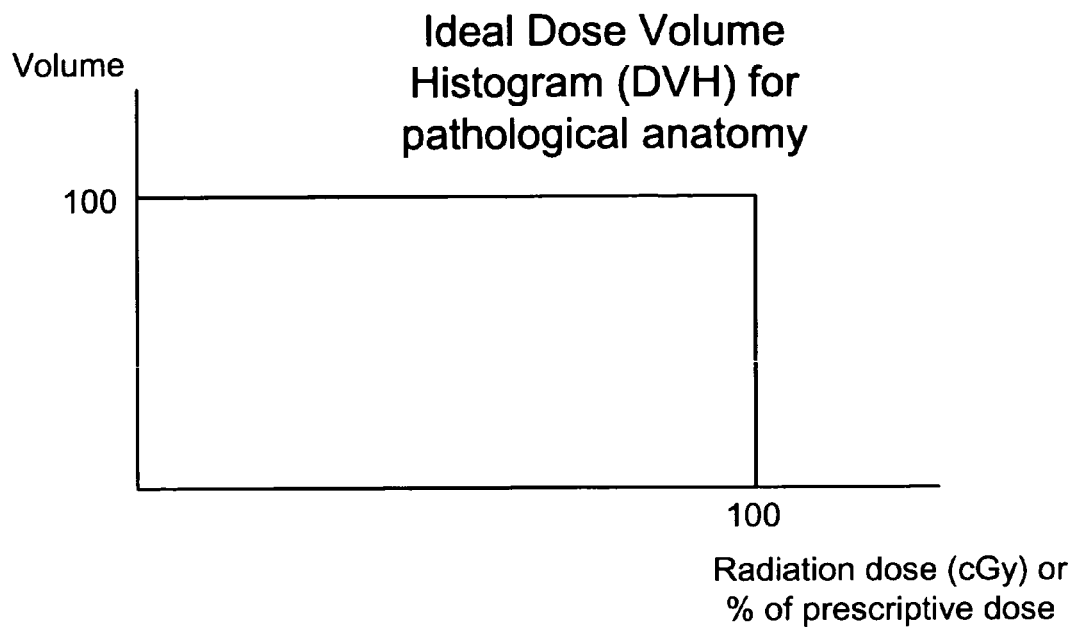
FIG. 2 illustrates one embodiment of an ideal DVH for a pathological anatomy.
Figure 3:
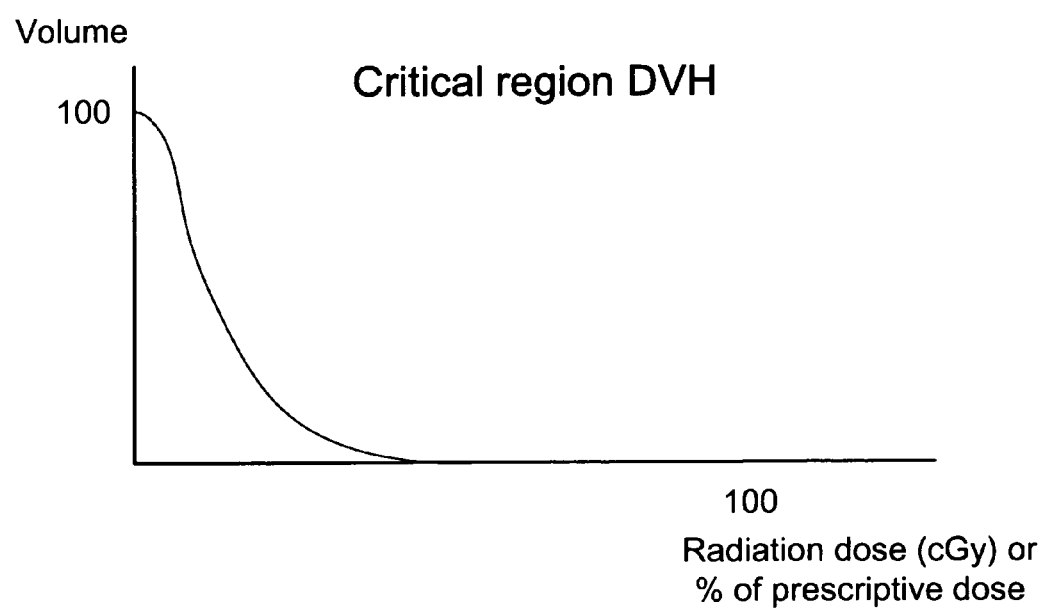
FIG. 3 illustrates one embodiment of a desirable DVH for a critical region.

In the following description, numerous specific details are set forth such as examples of specific systems, components, methods, etc. in order to provide a thorough understanding of the present invention. It will be apparent, however, to one skilled in the art that these specific details need not be employed to practice the present invention. In other instances, well-known components or methods have not been described in detail in order to avoid unnecessarily obscuring the present invention.

Embodiments of the present invention include various steps, which will be described below. The steps of the present invention may be performed by hardware components or may be embodied in machine-executable instructions, which may be used to cause a general-purpose or special-purpose processor programmed with the instructions to perform the steps. Alternatively, the steps may be performed by a combination of hardware and software.

The treatment planning software and system discussed herein may be implemented using hardware, software, firmware or combinations thereof. The software discussed herein may be written in a variety of programming languages, such as, for example, C/C++ and/or Assembly, etc. The operating system (OS) on which the software runs may be a Windows® OS from Microsoft Corporation of Washington or a Mac OS from Apple Computer of California. Alternatively, the OS may be a Unix, Linux, or other operating systems (e.g., embedded or real-time operating system), etc. The software and OS may be run on any type of platform, for example, a personal computer (PC) platform, workstation, etc.

The software, or computer program product, may include a machine-readable medium having stored thereon instructions, which may be used to program a computer system (or other electronic devices) to perform a process. A machine-readable medium includes any mechanism for storing or transmitting information in a form (e.g., software, processing application) readable by a machine (e.g., a computer). The machine-readable medium may include, but is not limited to, magnetic storage medium (e.g., floppy diskette); optical storage medium (e.g., CD-ROM); magneto-optical storage medium; read-only memory (ROM); random-access memory (RAM); erasable programmable memory (e.g., EPROM and EEPROM); flash memory; electrical, optical, acoustical, or other form of propagated signal (e.g., carrier waves, infrared signals, digital signals, etc.); or other type of medium suitable for storing electronic instructions.

Embodiments of the present invention may also be practiced in distributed computing environments where the machine-readable medium is stored on and/or executed by more than one computer system. In addition, the information transferred between computer systems may either be pulled or pushed across the communication medium connecting the computer systems, such as in a remote diagnosis or monitoring system. In remote diagnosis or monitoring, a user may utilize embodiments of the present invention to diagnose or monitor a patient despite the existence of a physical separation between the user and the patient. In addition, the treatment delivery system may be remote from the treatment planning system.

The treatment planning software may include various means to provide user interface, for example, click buttons, data entry fields, cascade buttons, dials, sliders, pull-down menus, click-and-drag, etc. At times a single type of user interface means may be discussed in regards to a particular function only for ease of explanation purposes and is not meant to be so limited. Other user interface means than the one(s) specifically discussed for a particular function may be used.

A method and apparatus for treatment planning are described, which includes treatment planning software (referred to as "TPS" herein). With its unique real-time optimization feedback process, the TPS allows clinicians to make adjustments during plan optimization, an advancement that significantly accelerates the creation of treatment plans. The TPS's advanced image fusion capabilities may enable clinicians to fuse images automatically or manually from multiple modalities, including CT, magnetic resonance (MR), positron emission tomography (PET), and 3D Rotational Angiography (3DRA). Together with an intuitive user interface and real-time feedback during the image fusion process, the TPS may provide clinicians with the tools they need to create rich patient models that are essential for accurately defining regions of interest during treatment planning.

In one embodiment, contouring of complex volumes of interest (VOIs) is made simple and efficient with the drawing and 2D/3D auto segmentation tools. Lesions and critical structures of all sizes—large, small or odd shaped—can be contoured in seconds. In one embodiment, a familiar Windows®-based display format and high-resolution graphics may be used to display features and help clinicians to accelerate the treatment planning process with accuracy and confidence. Alternatively, other types of display formats may be used.

In one embodiment, the TPS's selection of interactive tools and an "at-a-glance" display allows clinicians to observe and easily respond to feedback throughout the plan optimization process, assuring the desired result is achieved quickly and efficiently. Offering unparalleled flexibility, in one embodiment, the TPS supports isocentric, conformal, and/or mixed isocentric with conformal inverse planning methods to treat lesions throughout the body. In one embodiment, with one or both of two distinct planning optimization algorithms (e.g., iterative and non-iterative), the TPS assures that clinicians can maximize the unparalleled flexibility of the treatment planning system.

The TPS's ultra high 3D graphics make it possible for clinicians to visualize treatment doses at extremely high resolution. In one embodiment, the TPS offers a full range of evaluation and visualization tools: multi-slice view, color filtering and side-by-side plan comparison.

In one embodiment, the TPS is implemented on the Windows XP® product platform (alternatively, other operating system platforms may be used). The TPS may be designed for use with an image-guided, robotic-based radiation treatment system (e.g., for performing radiosurgery) such as the CyberKnife® system developed by Accuray Incorporated of California. Alternatively, the TPS may be used with another type of treatment delivery system, for example, a gantry based (isocentric) intensity modulated radiotherapy (IMRT) system or a stereotactic frame system having a distributed radiation source (e.g., a cobalt 60 gamma ray source) such as the GammaKnife®, available from Elekta of Sweden.

In one embodiment, the TPS is fully compliant with the DICOM 3.0 standard for the distribution and viewing of medical images and the DICOM-RT standard for viewing radiotherapy information overlain on medical images, and the TPS is pre-configured with these utilities and requires no additional software.

In one embodiment, to create a treatment plan, the user interface of the TPS may be organized, for example, into six planning tasks.

(1) LOAD. The user selects and loads patient data.
(2) FUSE. If the user chooses two or more medical images (e.g., different types of image modalities such as CT and PET images) to generate a treatment plan, this task allows the user to fuse, or visualize (e.g., by overlaying or otherwise combining), the images so they are aligned to the same physical space.
(3) ALIGN. The user sets the treatment modes, identifies fiducials, and aligns the nominal patient position within the detectors of the imaging system.
(4) CONTOUR. The user contours anatomical volumes of interest.
(5) PLAN. The user can generate and modify isocentric and non-isocentric plans. The user can also evaluate the dose distribution for the plan.
(6) VISUALIZE. The user can view an array of the two-dimensional image slices or merge and filter volume renderings of the patient anatomy.

In one embodiment, the TPS may also include ancillary tasks, for example, that provide advanced plan evaluation tools, system quality assurance tools, preference settings, and on-line assistance.

(7) Plan Quality Assurance. The user can compare two potential plans for the same treatment. The user can also sum two or more plans for the same patient. The user can display the dose distribution for the plan as treated to a phantom during a film test. The user can animate robot delivery of the treatment plan.
(8) Settings. This task includes a tool to center the dose distribution for a ball-cube plan. The interface displays the list of beams and their geometric patterns for the current plan. The user can set color preference for the isodose curves, VOIs, and screen overlays. The user can also set the behavior of the zoom and pan controls.
(9) Help. A user manual for the TPS can be accessed online.

Figure 4:
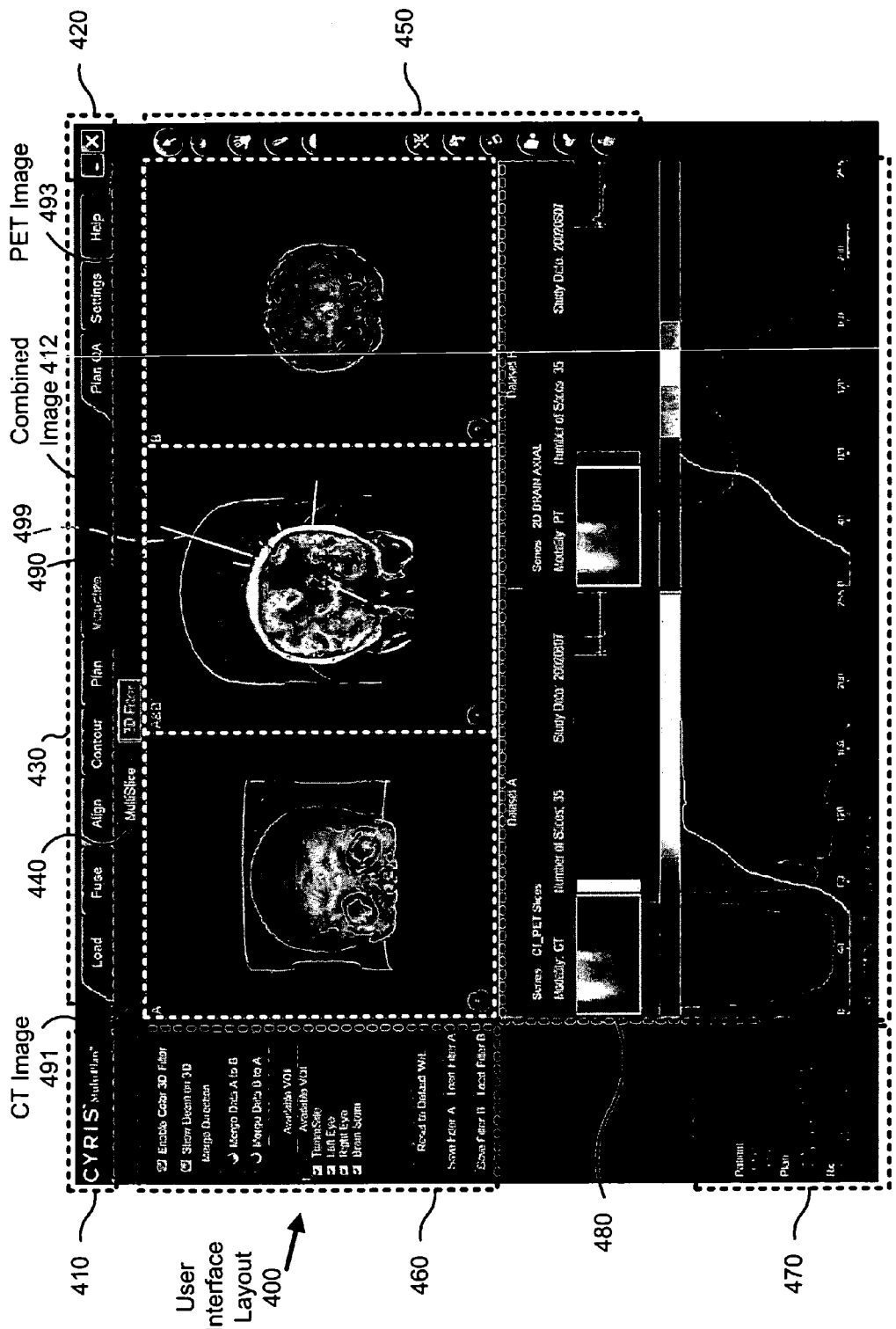
FIG. 4 illustrates one embodiment of a treatment planning software user interface layout.

FIG. 4 illustrates one example of a TPS user interface layout 400. In one embodiment, the screen layout of the user interface is divided into, for example, seven areas. In this exemplary embodiment, the seven areas on the screen layout include:

(1) Identification. The top left area 410 identifies the TPS as part of a particular product line (e.g., CyRIS™ product line). The top right area 420 includes minimize and exit controls.
(2) Task/Step Control. In one embodiment, the top menu bar 430 lists the tasks (e.g., Load, Fuse, Align, Contour, Plan, and Visualize). Below the menu bar 430 is an area 440 with a list of the steps contained in a selected task.
(3) Global Controls. Along the right side of the display are the global controls 450 that permit the user to access functions that may be desired during any of the steps in the planning workflow.
(4) Control View. The middle left of the display includes the controls 460 available for the currently selected step (e.g. Visualize). Each step may have a different set of controls.
(5) Display View. The large display center area 490 includes the display of the medical images and other large graphical and text controls. In the exemplary illustrated embodiment of FIG. 4, the user interface layout 400 includes a CT image 491, a PET image 493, and a combined CT/PET image 492. The CT/PET image may be combined with a fusion process to display the images in a common space. In one embodiment, the combined CT/PET image may also include a display of the beam paths (e.g., beam path 499) that are generated according to the treatment plan.

In one embodiment, the beam paths may be displayed on the combined CT/PET image using a combination of a volume rendering technique and a VOI rendering technique. A volume rendering technique can be used to present not only surface characteristic of an object, but also internal structures of the object. Volume rendering can convert an object into small voxels in 3D volume, and then assign each voxel with color and opacity info. The final rendering result is a 3D projection composition of the volume along a view direction. Any one of various volume rendering algorithms known in the art may be used. In one embodiment, for example, a 3D texture based direct volume rendering algorithm may be used. Since most of the latest graphics cards for PC platforms support 3D texture, volume rendering can be implemented at very low cost. Volume rendering is known in the art, for example, as discussed in "Volume Rendering in Radiation Treatment Planning" by Marc Levoy, et al. and "Three Architectures for Volume Rendering" by Jurgen Hesser et al., Eurographics '95, Volume 14, Number 3, 1995.

A VOI inside an object volume is defined as a geometry object. In radiosurgery applications, for example, tumor and critical structures can be defined as a volume of interest based on the patient image, such as CT or MRI. Volume rendering can render both volume and VOI info. There are different ways to render VOI information on top of volume information. In one embodiment, embedded geometry rendering may be used, which uses surface rendering technique to render the embedded geometry information into the volume rendering image. In an alternative embodiment, VOI information may be rendered on top of volume information by converting the VOI geometry to special volume information before the rendering. The VOI and volume information is rendered by using a volume rendering method at the same time.

In another embodiment, the combined image may also include a display of other treatment parameters, for example, a VOI structure and a dose contour. It should be noted that, alternatively, types of images of CT and/or PET may be displayed (e.g., MRI, ultrasound, etc.) Each step may have a different display layout. For some steps, the user may be able to select the display layout.

(6) Patient Identification. The bottom left area 470 displays patient and plan information, including patient name and medical ID, plan name, date and time the plan was saved, and the prescription percentage and dose.

(7) Status. The bottom center and right areas 480 display status. The position of the image focus and value of the image gray scale number appear on the right. On the left is general information, including a time-elapsed bar.

In one embodiment, the TPS provides a user with a 3 tier task/step/function workflow-based approach to treatment planning in which the user is forced to perform a certain enabled task (e.g., fuse), steps within the task (e.g., the seed points and register steps of the Fuse task), and functions within the step (start and pause function of Register step), by being provided a view that only enables the user to interface with the certain enabled task (e.g., a preceding task), before the user is given the ability to perform another task (e.g., a proceeding task) in the TPS by being provided another user interface view corresponding to the other task. Alternatively, the user may be allowed to perform one or more of the tasks, or steps within a task, out of sequence or before completing other tasks and/or steps. Details of each of the exemplary tasks and their associated steps and functions are discussed below.

Load Task

Figure 5:
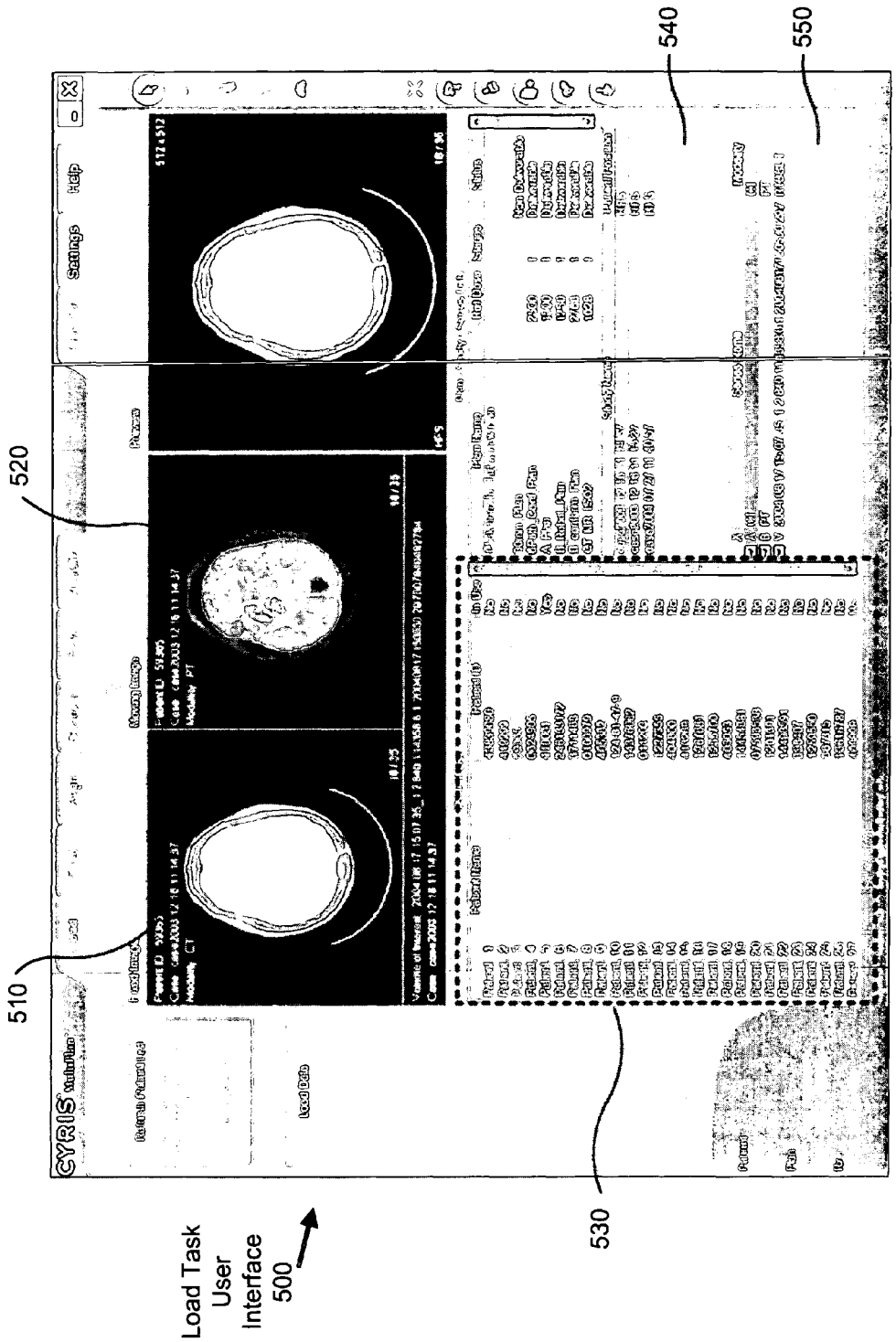
FIG. 5 illustrates one embodiment of a load task user interface.

FIG. 5 illustrates a user interface for the Load task 500. In one embodiment, the Load task is the first step of the TPS. This task allows the user to load previously saved plans, start a new plan by loading DICOM formatted patient data, including volumes of interest pushed as DICOM RT structure sets, recover the last plan worked on, or delete a previously saved plan. For exemplary purposes only, the following method of creating a treatment plan using the TPS is described with respect to a newly created plan. To start a new plan, the user selects "Click here to start a new plan" near the top of the plan list, as well as selecting the patient for the treatment plan (e.g., Patient 3 as highlighted in FIG. 5).

The user interface of FIG. 5 also displays a fixed image 510 and a moving image 520. For example, the fixed image 510 may be a CT image and the moving image 520 may be a MR or PET image. The use of multiple image modalities is beneficial for treatment planning. A CT image may be selected because its data is used to track patient movement. MR or PET images may provide improved views of the pathological anatomy compared to CT images. The fixed and moving images correspond to the selected patient. For example, once a particular patient is selected from the patient list 530, a list of studies corresponding to that patient is displayed in study list 540. Then for each study selected, a list of images is displayed. The fixed medical image 510, for example, a CT image, may be selected by first the desired study from the study list 540 and the desired CT image from the image list 550. As with the fixed image, the user selects the moving image 520 by first selecting the patient, study, and list of images.

Fuse Task

With the fixed image 510 and moving image 520 loaded by the TPS, the next step is to fuse, or visualize (e.g., by overlaying or otherwise combining), the images together. In order for the user to contour structures such as the pathological and critical structures, the fixed and moving images are aligned together in a common space so that one image can be overlaid over the other image. In one embodiment, the fixed (e.g., CT) image 510 and the moving (e.g., MR) image 520 may be three-dimensional reconstructions when viewed on the display. The fusing of two image modalities first involves selecting multiple seed points that are approximately in similar places for both images, in order to get an idea of how the two images initially align.

Figure 6:
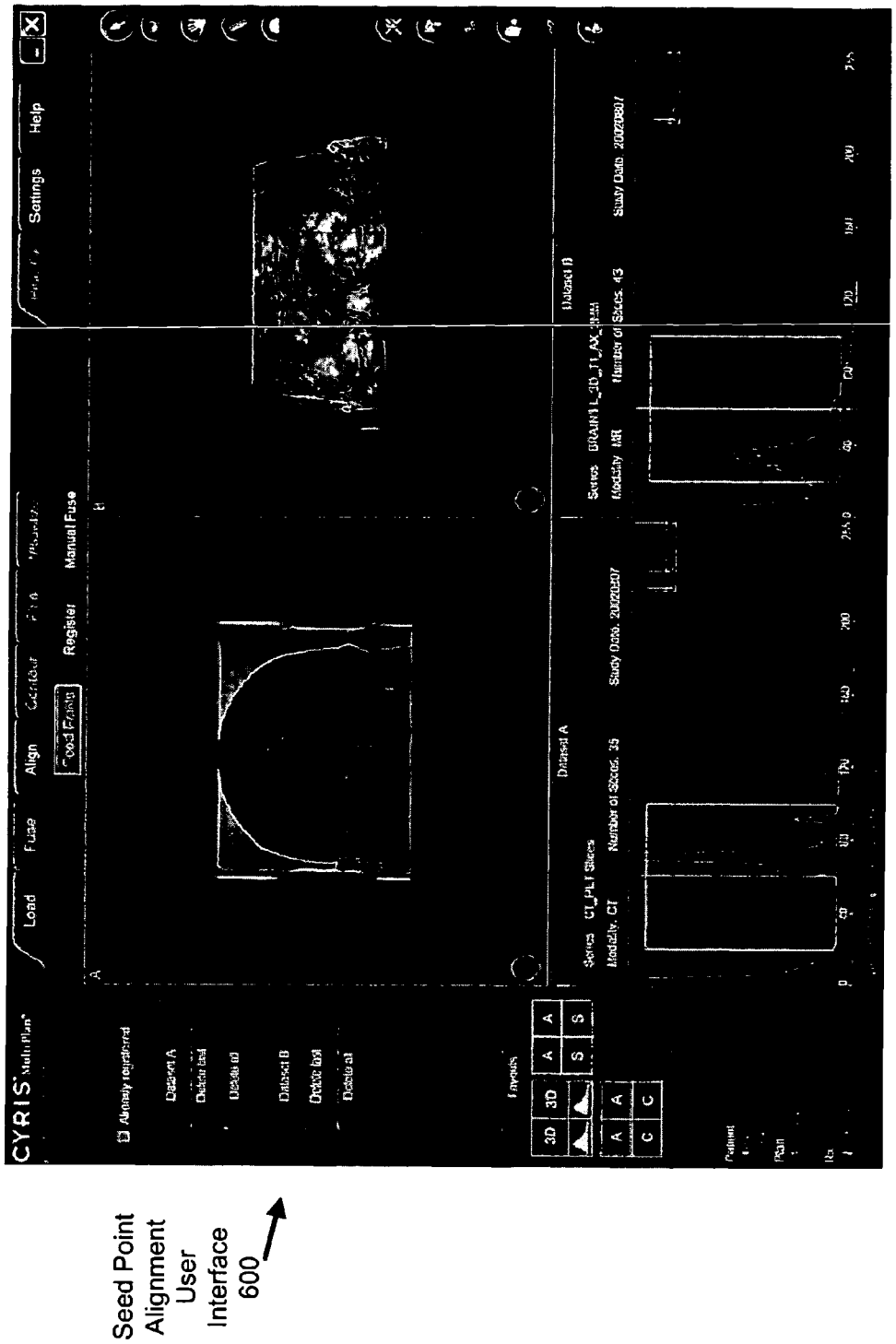
FIG. 6 illustrates one embodiment of a seed point alignment user interface.

FIG. 6 illustrates a user interface 600 of a CT image and a MR image with three seed points selected, including the left and right eyes, and a point located near the forehead. When the seed points have been selected in the fixed and moving images, the Register step is enabled in the TPS. Registration involves the transformation that maps one image to another and, in particular, that maximizes the mutual information of the two loaded images. Once this transformation has been determined and the registration has been completed, the images may be visually fused onto a common coordinate space as discussed below.

Figure 7:
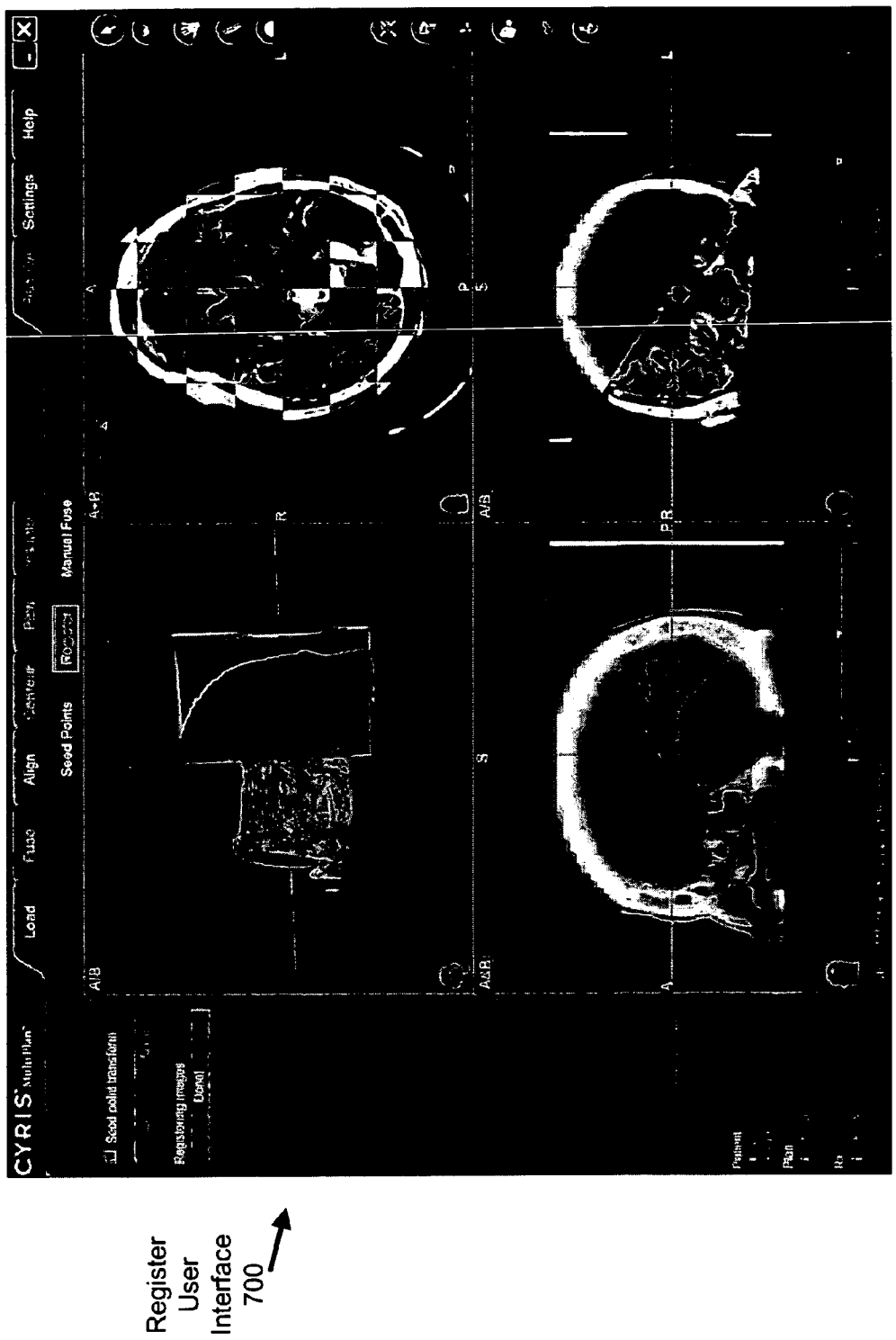
FIG. 7 illustrates one embodiment of a registration user interface.

The windows in the bottom left and right of the seed point alignment user interface 600 contain the three-dimensional filter controls for the fixed and moving images, respectively. These controls operate on the opacity of the image. As such, anything in the image having intensity less than that of the left hand side of the rectangle is transparent in the volume rendering. Anything with intensity greater than that of the right hand side is fully opaque. By manipulating the three-dimensional filter, different structures in the image may be hidden or highlighted. By selecting the Register button, the user-interface of FIG. 7 is displayed, which includes one three-dimensional and three two-dimensional split views. The fixed and moving images are fused by employing a matrix algebra solution that performs an initial alignment of the two images based on the selected seed points from each image. The user may then have the TPS perform a refinement process after the initial Register step. By selecting the "Start" button, the TPS executes an algorithm to improve the alignment of the two images. During the refinement process, the user can manipulate the split views to evaluate the quality of the fusion. It should be noted that the fusion process encompasses the three-dimensional volume of the images displayed in FIG. 7. Two-dimensional images are used merely to show the result of the fusion process, but the actual optimization is performed on the four three-dimensional volumes. It should also be noted that fusion of the fixed and moving images may be performed without the use of seed points. The images may be taken as they are and fused either manually or with the algorithm of the TPS.

Figure 8:
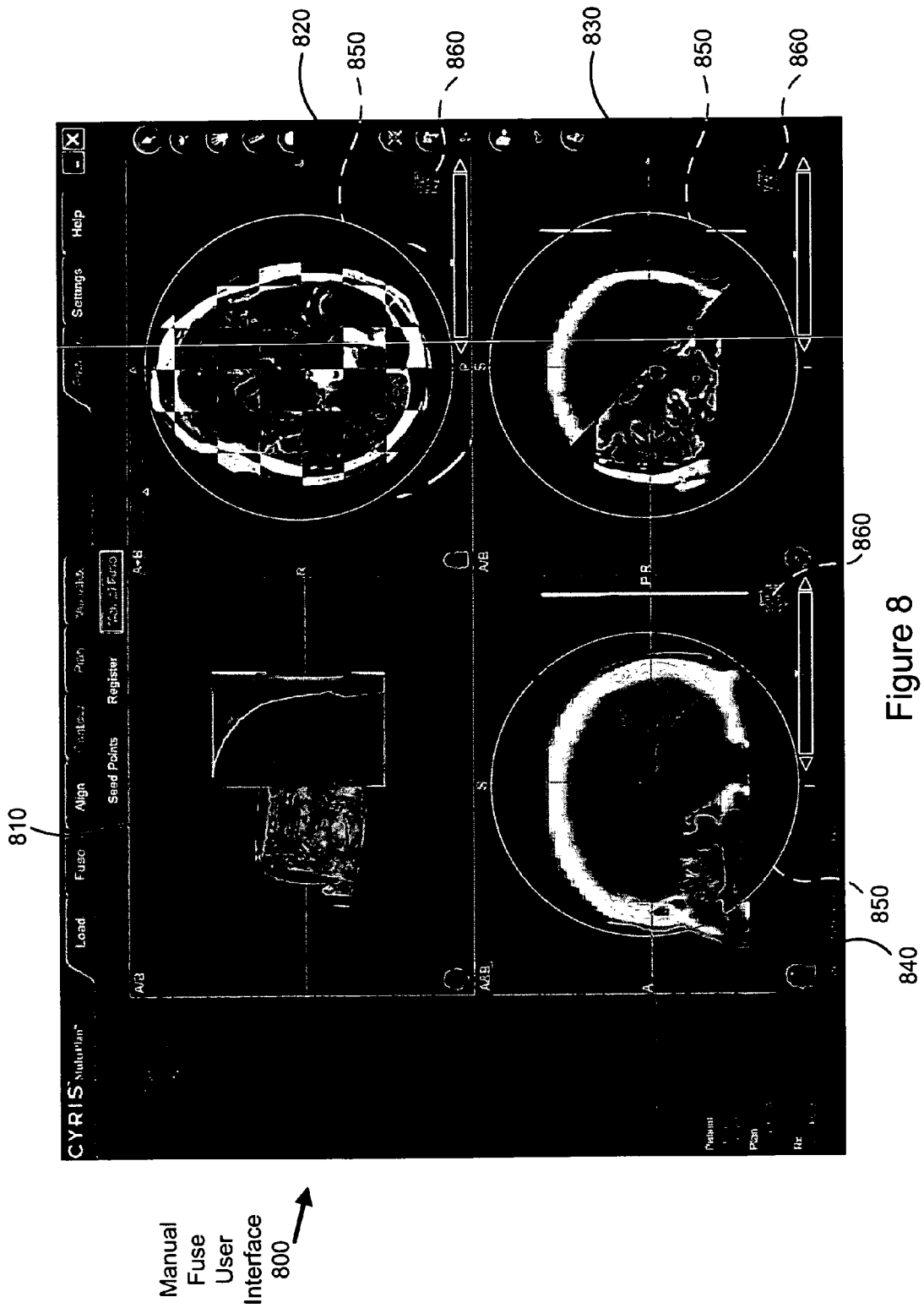
FIG. 8 illustrates one embodiment of a manual step user interface.

FIG. 8 illustrates one embodiment of a manual fuse user interface. If the automatic fusion process performed by the TPS is not satisfactory (or the user wants to either supplement or supplant the automatic fusion process), the user may perform a manual fusion process using additional tools provided by the TPS. For example, for a spine study, the CT image is obtained with the patient lying in one particular position, and the MR image is obtained with the patient lying in a different position. Because the images were obtained using different positions, the automatic fusion process may not be possible because it is difficult to match the two images together rigidly.

In one embodiment, the manual fuse user interface 800 may include a 3D display of the fusion process as the fusion is progressing. The interface 800 may also include a checkerboard view (A+B) 820 having a checkerboard mosaic of two the different modality images (e.g., CT and MR); a split diameter mosaic (A/B) view 830 of two the different modality images; and an overlay (A&B) view 840 of the two different modality images. The checkerboard view 820 displays a quilt-like pattern of fixed and moving images. In one embodiment, the size of the checkerboard may be controlled by a slider at the top right with the value of the slider being the edge length of each patch in screen pixels. In the split diameter mosaic 830 includes an oblique line that can be rotated by the user about its axis of rotation to change the modality used to display different areas of the view. The point of rotation is the intersection of the focus lines. In one embodiment, the user can click and drag a mouse to move these lines. The overlay views 840 displays the fixed and moving images at different opacity levels. In one embodiment, the user may set the color of the moving image in the overlay view from a secondary overlay pulldown window.

In the manual fusion process, the user can translate or rotate the moving image in any of the three planar views. Gross changes may be made to the transformation of an image as well as fine changes. This allows the user to align the images correctly near the target position even though they may not be correct in other regions of the images.

In one embodiment, the curser may be dragged to make gross changes to the transformation. In one embodiment, the circle 850 in the view defines the boundary of the translation and rotation portions of the screen. Inside the circle 850, cursor movements translate the moving image and outside the circle, cursor movements rotate the moving image. Alternatively, other shapes (e.g., oval, square, etc.) may be used to define the boundary.

In one embodiment, fine motion is controlled with the arrows 860 at the bottom right of each planar view 820, 830 and 840. The straight arrows translate the image one pixel (in screen coordinates) in the indicated direction. The arced arrows rotate the image one pixel in the indicated sense.

Align Task

Figure 9:
FIG. 9 illustrates one embodiment of a set treatment parameters user interface.

FIG. 9 illustrates one embodiment of a user interface for setting treatment parameters. After fusion of fixed and moving images is completed, the next step is to establish parameters that describe the treatment to be performed on the patient. In one embodiment, the user is forced to set a particular enabled parameter (e.g., a preceding parameter) before the user is given the ability to set another parameter (e.g., a proceeding parameter) in treatment parameters setting user interface 900.

For example, the first parameter may be the total number of stages in the treatment 910. In radiosurgery, the overall treatment is typically divided into a set of steps instead of giving the patient the entire radiation dose in one session. This is referred to as "fractionation." For example, the total treatment dose may be divided over five treatment sessions, because there may be critical structures adjacent to the pathological anatomy that may not be able to tolerate the total radiation dose if performed in one session. By dividing the treatment into multiple sessions, the critical regions that may be exposed to radiation are given time to recover and heal to a certain extent. Depending on the dose delivered to the patient, it may not be necessary to divide the treatment into multiple sessions. Here, the user is allowed to define the number of treatment stages, for example, by typing in a number or incrementing or decrementing the number of stages using the '+' or '−' buttons.

In one embodiment, the next parameters that the treatment parameters setting user interface 900 may allow the user to set, in sequence, are Treatment Anatomy 920 and Template Path Set (e.g., 800) 930. Treatment Anatomy 920 informs the treatment planning and delivery system of the general anatomical area (e.g., head) to be treated. In the illustrated embodiment, the treatment anatomy is "head." Path Set 930 defines the set of positions (e.g., 800 illustrated) for the robotic arm (e.g., robotic arm 4052) from which to activate the radiation beam from the LINAC. The TPS may provide a number of templates with different sets of beam positions, depending on the treatment anatomy selected. In one embodiment, two cascade buttons provide the user interface means to select the Treatment Anatomy 920 and Template Path Set 930.

In one embodiment, the next parameters that the treatment parameters setting user interface 900 may allow the user to set, in sequence, are Tracking Method option 940 and Treatment Mode 950. Tracking Method 940 (e.g., 6D_Skull) defines how the imaging system automatically takes x-ray shots of the patient while the patient is being treated, and the treatment delivery system uses the data from the x-ray images to determine the exact position of the patient during treatment, allowing the robot to make adjustments in case the patient moves during treatment. Treatment Mode 950 (e.g., automatic or manual) allows the treatment delivery system to control the timing for the diagnostic images and the firing of individual beams. Alternatively, the user may instruct the system to take diagnostic images and fire individual beams.

In one embodiment, the next parameter that the treatment parameters setting user interface 900 may allow the user to set is Maximum Beam On Time 960. This option allows the user to set the maximum duration that a single beam is on. For example, the value may be set to the length of time that the patient is expected to hold his or her breath during treatment. The value can also be used where a specific limit of beam-on time is desired between diagnostic x-rays.

In one embodiment, the last parameter that the treatment parameters setting user interface 900 may allow the user to set is SST mode that is only available when the user chooses Skeletal Structure Tracking (SST) as the tracking method. With this option, the user indicates the anatomical regions being treated, for example, cervical spine (CSPINE) thoracic spine (TSPINE) and lumbar spine (LSPINE).

It should be noted that in alternative embodiments, the treatment parameters setting user interface 900 may allow the user to set the above described parameters in other orders and/or may allow the user to set parameters other than the exemplary parameters discussed above.

Figure 10:
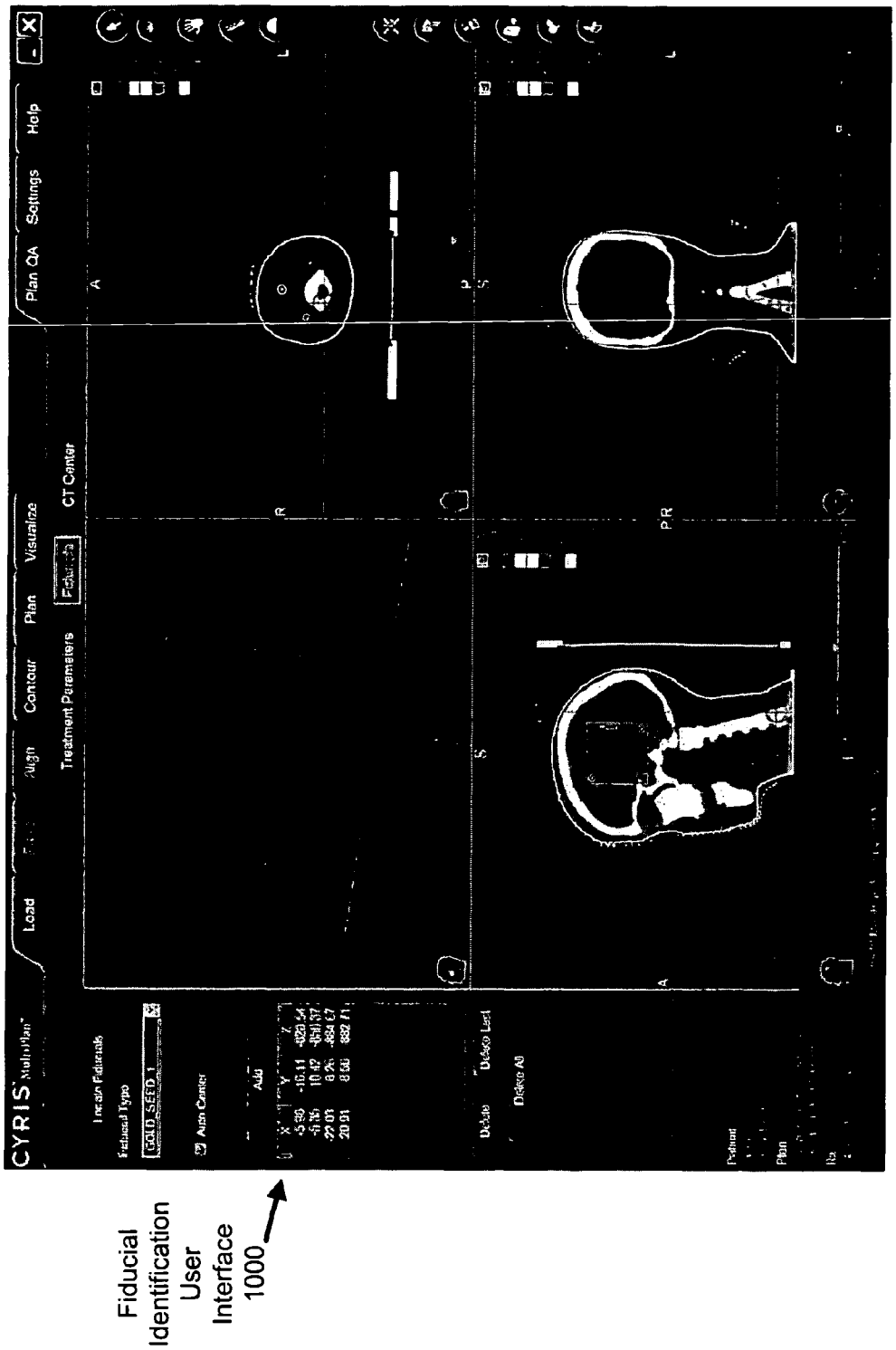
FIG. 10 illustrates one embodiment of a fiducial identification user interface.

FIG. 10 illustrates one embodiment of a fiducial identification user interface. In one embodiment, after setting the treatment parameters, a Fiducial window may be enabled to identify at least one or more fiducials. Although fiducials may not be used in cranial region treatments, a discussion is provided with respect to fiducials implanted in body or spinal treatments. The display of FIG. 10 includes a three-dimensional view and three planar views (axial, coronal, and sagittal). The user first selects the type of fiducial (e.g., Gold_Seed_1) implanted in the patient. The user then selects whether to use Auto Center mode or manual placement mode. In Auto Center mode, the center of the fiducial is placed by finding the center of the gray-scale intensity around a small volume near the location where the fiducial is located. A fiducial may then be added to any of the three planar windows using a cursor. Once added, a fiducial appears as a marker in the two-dimensional views. The location of an identified fiducial may also be moved by dragging the marker in either the two-dimensional or three-dimensional views.

Figure 11:
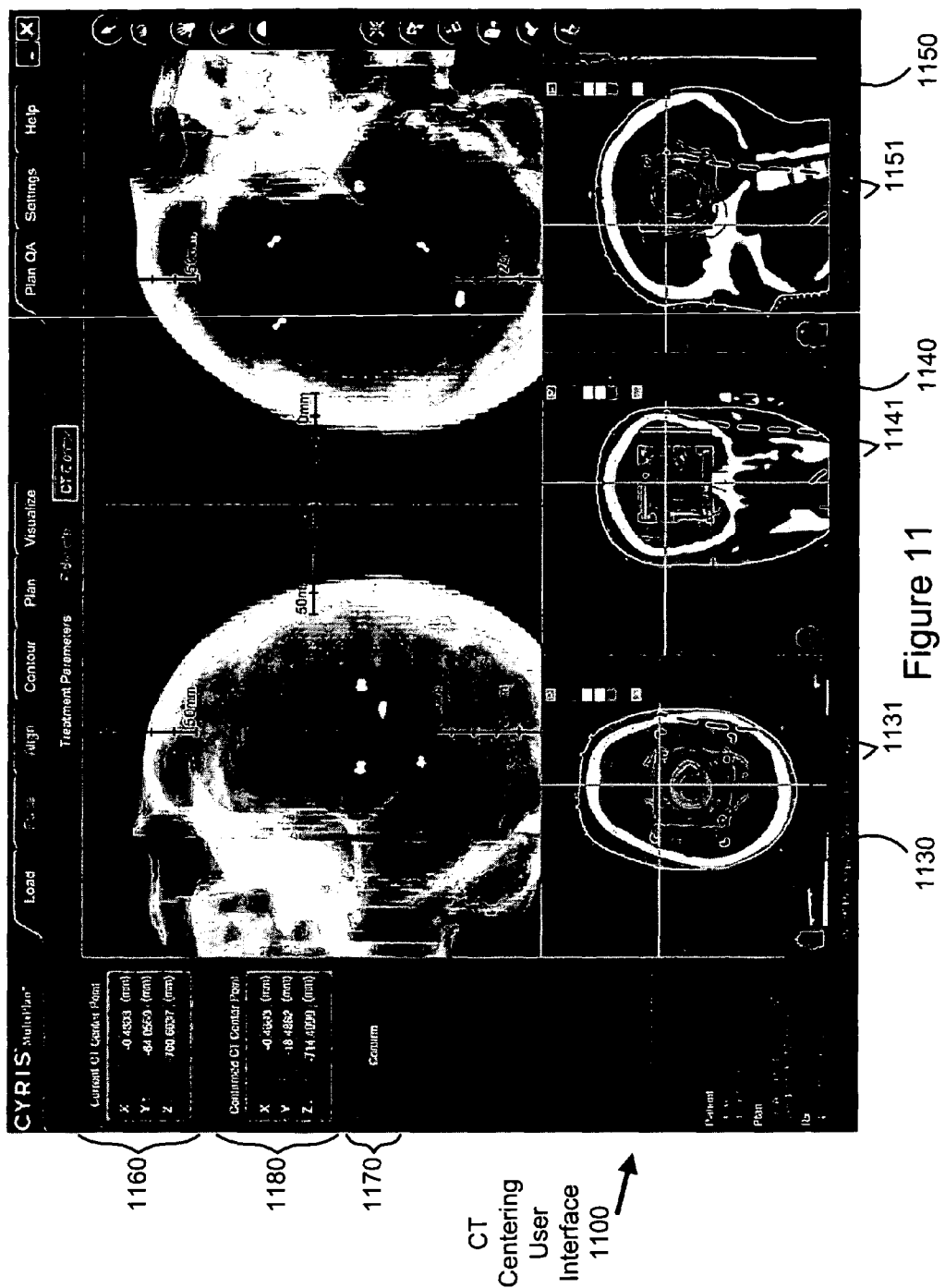
FIG. 11 illustrates one embodiment of a CT centering user interface.

FIG. 11 illustrates one embodiment of a CT centering user interface 1100. During treatment delivery, the machine center should be aligned with the CT image so that the imaging system may function correctly. This is accomplished by defining the CT image center and the position of the patient during treatment. In one embodiment, the position of the patient on the treatment couch is used to define the CT center. The top two windows 1110 and 1120 are Digital Reconstructed Radiographs (DRRs) of the patient's head region, given the current machine center. A DRR is a reference image that may be rendered from CT images. More particularly, a DRR is a synthetic x-ray produced by combining data from CAT scan slices and computing a two-dimensional (2-D) projection through the slices that approximates the geometry of the imaging system. DRR is known to those of ordinary skill in the art; accordingly, a more detailed discussion is not provided. The bottom three windows 1130, 1140 and 1150 are the axial, coronal, and sagittal two-dimensional views of the patient's head region. The focus of these three windows 1130, 1140 and 1150 is the current CT center. In one embodiment, the cross-hairs 1131, 1141 and 1151 may be moved by the user to adjust the CT center in each of windows 1130, 1140 and 1150, respectively. In one embodiment, as the user moves the CT center, the Current CT Center Point coordinates will appear in the control view 1160. As the user moves the CT center in one window, the TPS may automatically re-display the CT center in other views (e.g., the DRR window 1110 and/or 1120).

In one embodiment, the user must confirm the CT center (e.g., by clicking on a confirm button 1170) before the user can proceed to the Contour and Plan Tasks. In one embodiment, if the coordinates have been confirmed, the coordinates appear in the Confirmed CT Center Point table 1180. If the user needs to change the CT center, the user has to reconfirm the new CT Center of the plan will retain the original CT center in one embodiment.

By aligning the machine center with the CT center, the treatment delivery and imaging systems can produce the desired images (e.g., x-ray images) of the patient during treatment when the patient is properly aligned with the treatment delivery system.

Contour Task

The next task of treatment planning is creating and modifying anatomical volumes of interest. This task includes two steps: Delineate and Properties. The Delineate step includes drawing tools for the user to draw and edit volumes of interest. The Properties step allows the user to change specific tags and display settings associated with each volume of interest. The volume of interest (VOI) is a user-defined region overlain on the medical images that typically represents a distinct anatomical feature such as the pathological anatomy targeted for treatment or critical structures to avoid radiation. For example, using the moving image such as a two-dimensional MR image, the user identifies and designates the pathological anatomy as the target region by drawing or contouring a line around the pathological anatomy. This process may be repeated for additional two-dimensional slices of MR images. In one embodiment, the contour from one slice is reproduced on the next slice so that a bumper tool may be used to modify the contour without having to re-draw a new line. This process may be performed separately for the pathological anatomy and any critical structures.

The bumper tool is just one of several drawing tools available in the TPS. In an alternative embodiment, The TPS also includes a Smart Curve Fitting option, which is a contouring algorithm that can be used in conjunction with Pen, Line, Ellipse, and Bumper drawing tools. For example, the user first draws a line around the target to contour using the Pen tool. The Smart Curve Fitting algorithm will reshape the line around the target to fit the boundary based on the contrast within the display. This allows the user to draw a less than perfect line around the target during the initial stage of contouring.

Figure 12:
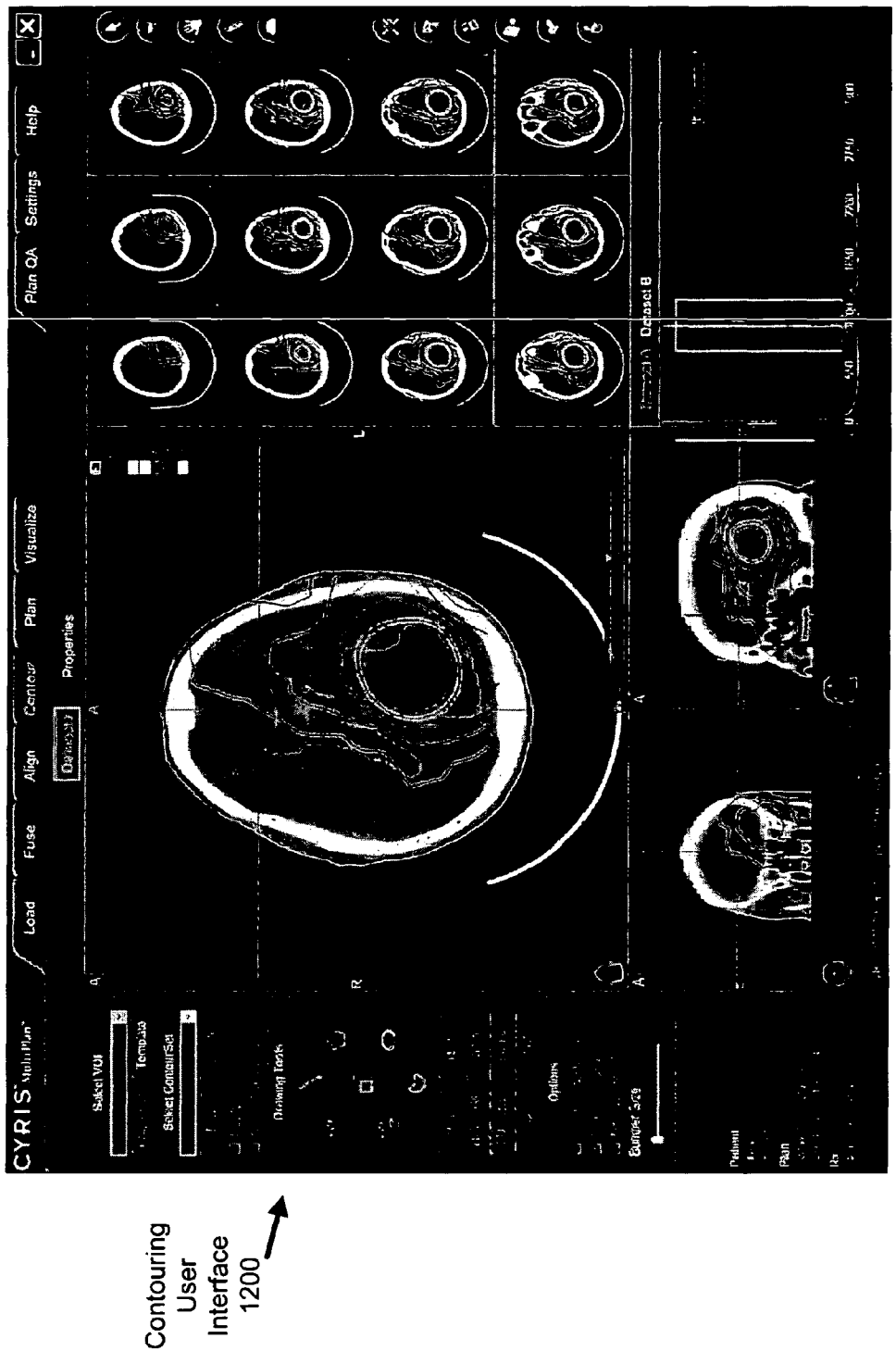
FIG. 12 illustrates one embodiment of a contouring user interface.

After contouring several slices, the TPS may perform an interpolation of all the two-dimensional slices for a particular image modality so that the operator does not have to contour each and every two-dimensional slice. For example, the TPS provides automatic interpolation to reduce the time required to generate a contour set. When a user draws a contour on one slice and a second contour on a second slice for the pathological anatomy, the contours for slices between the first slice and the second slice are automatically determined using linear interpolation. Interpolating all the slices for a particular type of image may not be appropriate for certain types of anatomical regions. For example, anatomical structures may change significantly from slice to slice may be too dramatic for the TPS to interpolate properly. In contrast, an anatomical structure such as the spinal chord that has fairly consistent dimensions from slice to slice may be interpolated accurately by the TPS, thereby reducing the number of slices that would require contouring. FIG. 12 illustrates an example of user interface for the contour step, showing the contoured target region (e.g., the pathological anatomy) and the critical region (e.g., brain stem).

Plan Task

Figure 13:
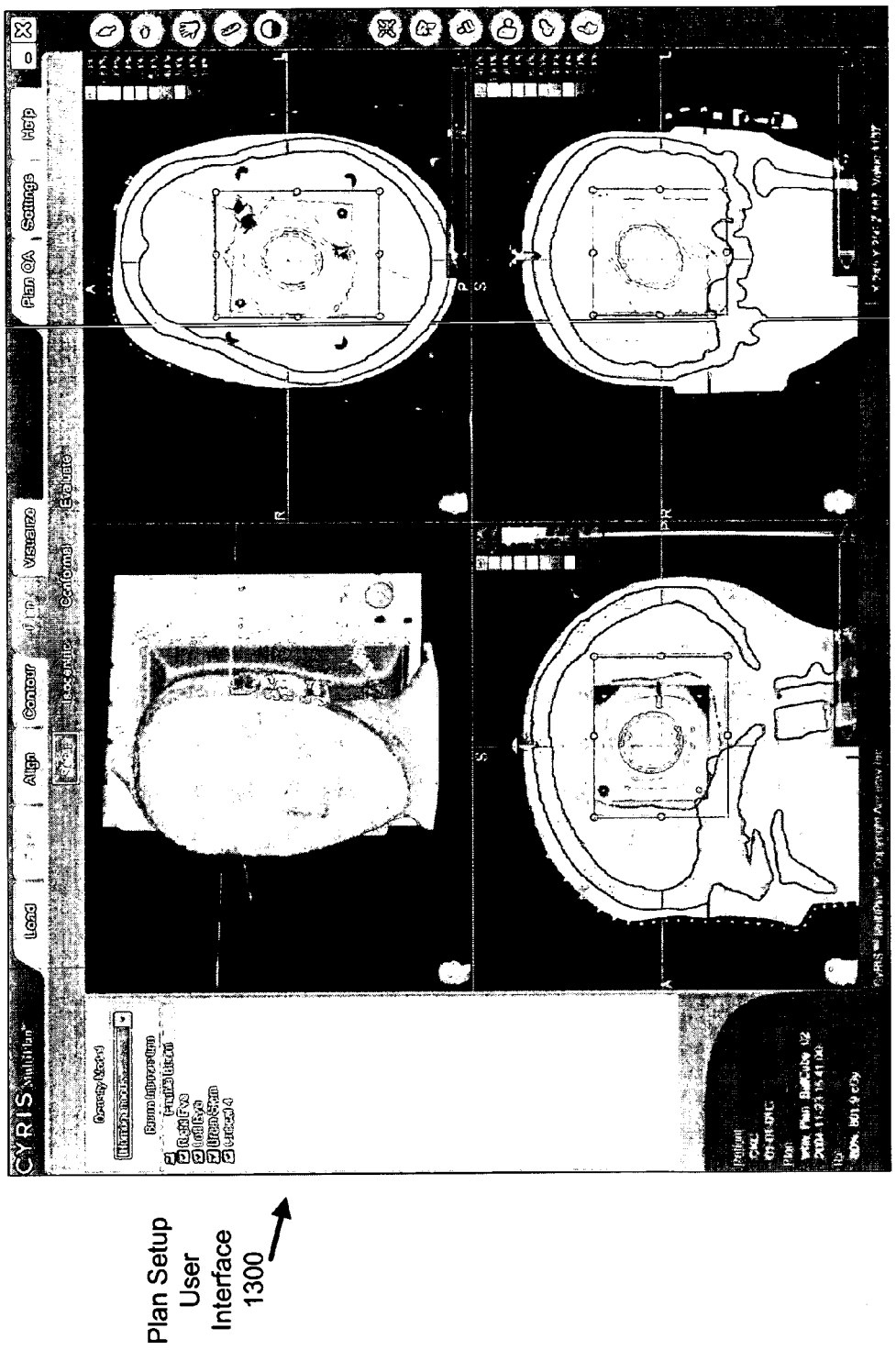
FIG. 13 illustrates one embodiment of a plan setup user interface.

The Plan task contains the functionality for creating, refining, and reviewing treatment plans. The TPS supports isocentric, conformal, and mixed isocentric/conformal planning. The first step of the Plan task is defining certain parameters that will be used in the treatment planning process. An example of the user-interface for setting up parameters is illustrated in FIG. 13. In this exemplary embodiment, one parameter is Density Model, which reflects the modeling of the radiation absorption by the tissue. Depending on the type of tissue being exposed to radiation, the plan should account for how the CT intensities map into absorption coefficients of radiation. For example, the homogenous model is selected for the cranial region because the tissue is fairly consistent. The homogenous model treats dark intensity regions as air so no radiation is absorbed, and everything else as one type of tissue, which is a fair assumption of the cranial region (i.e., the brain). Other predefined models that are available include Lung Standard and Body Standard.

Figure 14:
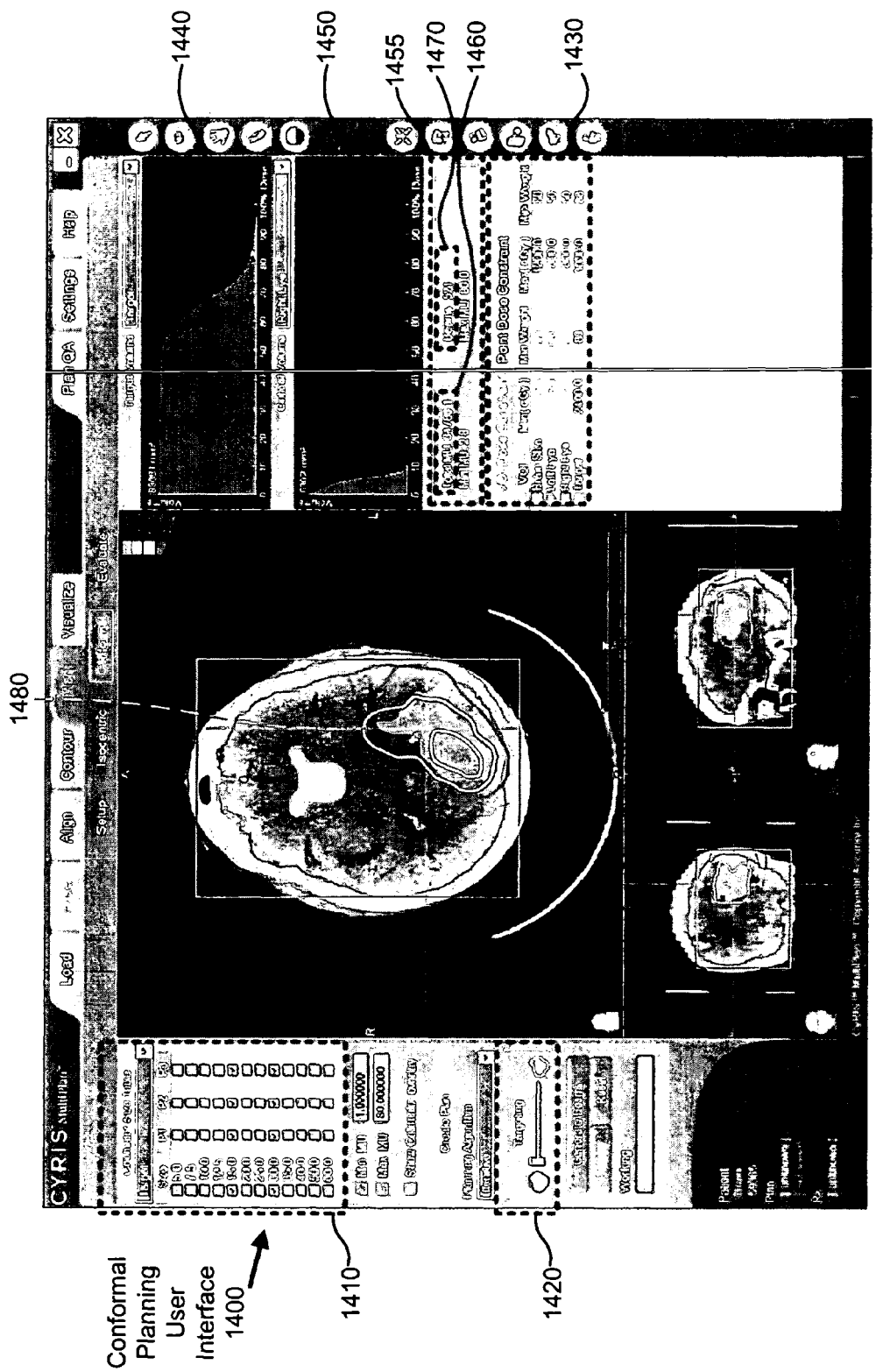
FIG. 14 illustrates one embodiment of a conformal planning user interface.

FIG. 14 illustrates one embodiment of a user interface for conformal planning. In conformal planning (so-called because of the goal of having the generated isocontours conform to the shape of the target), the TPS may use an iterative or non-iterative optimization algorithm to produce conformal plans giving a balance of homogeneity and conformality. In one embodiment, in order to start a conformal plan, at least one region designated as a target is defined. Conformal planning takes advantage of an image-guided, robotic-based radiation treatment system (e.g., for performing radiosurgery) such as the CyberKnife® system, because the LINAC positioning mechanism (e.g., robotic arm 4052 of FIG. 18) can move around freely with multiple degrees of freedom, allowing the radiation beams of the LINAC to point anywhere in space.

Figure 15:
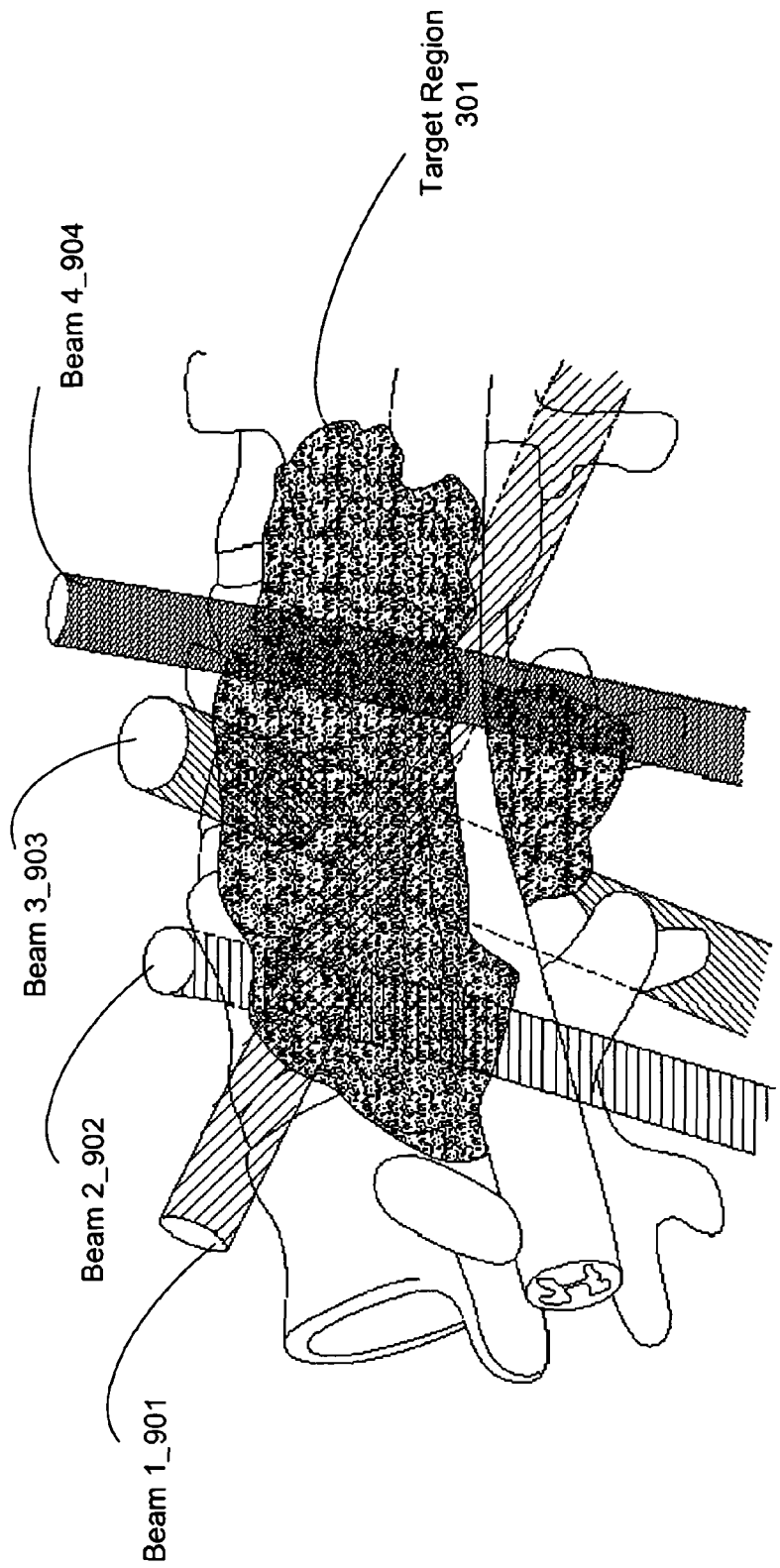
FIG. 15 illustrates a two-dimensional perspective of non-isocentric radiation beam delivery at a pathological anatomy.

FIG. 15 illustrates a two-dimensional perspective of non-isocentric radiation beam delivery at a target region based on conformal planning. It should be noted that four beams, beam_1 901, beam_2 902, beam_3 903, and beam_4 904 are illustrated in FIG. 15 only for ease of discussion and that an actual treatment plan may include more, or fewer, than four beams. Moreover, the four beams are representative of conformal planning, in which each beam passes through various points within target region 301 (e.g., the pathological anatomy). In conformal planning, some beams may or may not intersect or converge at a common point, and although the four beams appear to intersect in the perspective of FIG. 15, the beams may not intersect in their actual three-dimensional space. The radiation beams need only intersect with the target volume and do not necessarily converge on a single point, or isocenter, within the target 301.

In one embodiment, the initial beam weights may be a default beam weight determined by the operator or the TPS. The initial beam weights may also be influenced by the prescribed radiation dose to be delivered to target region 301. For example, if a total prescribed dose of 3500 cGy is set for target region 301, the TPS would automatically determine the beam weights for each beam to balance conformality and homogeneity to achieve that prescribed dose as closely as possible.

Referring again to FIG. 14, one parameter for conformal planning may be collimator size, which is provided by a collimator size table 1410. Collimator size refers to the thickness (e.g., diameter) of the radiation beam originating from the linear accelerator (e.g., LINAC 4051). For a selected target (e.g., pathological anatomy), a collimator size (e.g., 15.0, 30.0) and one or more paths (e.g., P1, P2, P3) available for that collimator size may be selected as illustrated in the exemplary table 1410. In one embodiment, another parameter is minimum/maximum monitor units (MU) allowed for the beams aimed at the selected target. The user also defines a minimum dose constraint for the target region and a maximum dose constraint for a critical region. For example, a minimum dose constraint of 2400 cGy is set for the target region and a maximum dose constraint of 1200 cGy is set for the right eye critical region, as shown in FIG. 14.

In one embodiment, the TPS may provide either of two types of algorithms for optimizing the dose distribution based on the user defined minimum/maximum dose constraints. One algorithm is an iterative algorithm that optimizes deviations above the maximum dose constraint and below the minimum dose constraint. The iterative planning algorithm first generates a set of beams and performs an initial dose distribution calculation, and subsequently attempts to improve the initial dose distribution calculation by altering one or more beams. Another algorithm performs convex optimization, for example the Simplex algorithm, which involves minimizing the number of MUs subject to the minimum/maximum dose constraints. A Simplex algorithm is known in the art; accordingly, a detailed description is not provided. Alternatively, other iterative and non-iterative optimization algorithms may be used.

In one embodiment, a combination of both algorithms may be used. For example, the plan optimization may begin with the Simplex algorithm to determine the minimal MU required, followed by the iterative algorithm. The Simplex algorithm may minimize the number of monitor units subject to the constraints and thereby require fewer monitor units than with the iterative algorithm. Weights set to 100 are exact constraints. Multiple exact constraints and/or a low value of a maximum dose may lead to issues. Relaxing these constraint weights (by setting the weight to a value less than 100) may improve the chances of finding a solution. The iterative algorithm optimizes deviations above maximum dose constraints and below minimum dose constraints. The penalty is based on the amount of deviation at each constraint point and the weight applied to each constraint. The iterative optimization may begin with a defined set of beam geometries. In one embodiment, as the optimization proceeds, beams with little dose may be retargeted to colds spots in the tumor in order to update the dose during optimization and re-optimize from the last configuration solved by the optimizer. The iterative algorithm may tend to achieve a more homogeneous solution. One embodiment of an iterative algorithm is discussed in U.S. patent application Ser. No. 11/145,121, which is incorporated by reference herein. After beginning with the simplex method and then, after finding the first solution, using the iterative method, may enable the user to refine the plan beginning with a minimal MU solution.

In one embodiment, the conformal planning user interface 1400 may include a targeting slider 1420, shown near the left side of the user interface of FIG. 14. The targeting slider 1420 allows the user to define the number of beams that will be aimed at points internal to the target, and the number of beams aimed at the boundary of the target. When the targeting slider 1420 is positioned completely to the left by the filled icon, all beams are aimed at points randomly chosen within the target. When the slider is positioned completely to the right by the un-filled icon, all the beams are aimed at the periphery of the target. An intermediate slider position instructs the TPS to split the beam set proportionately between the interior and exterior periphery. An alternative embodiment for a targeting slide directs beams at a surface a prescribed distance either internal or external to the target volume.

Figure 19:
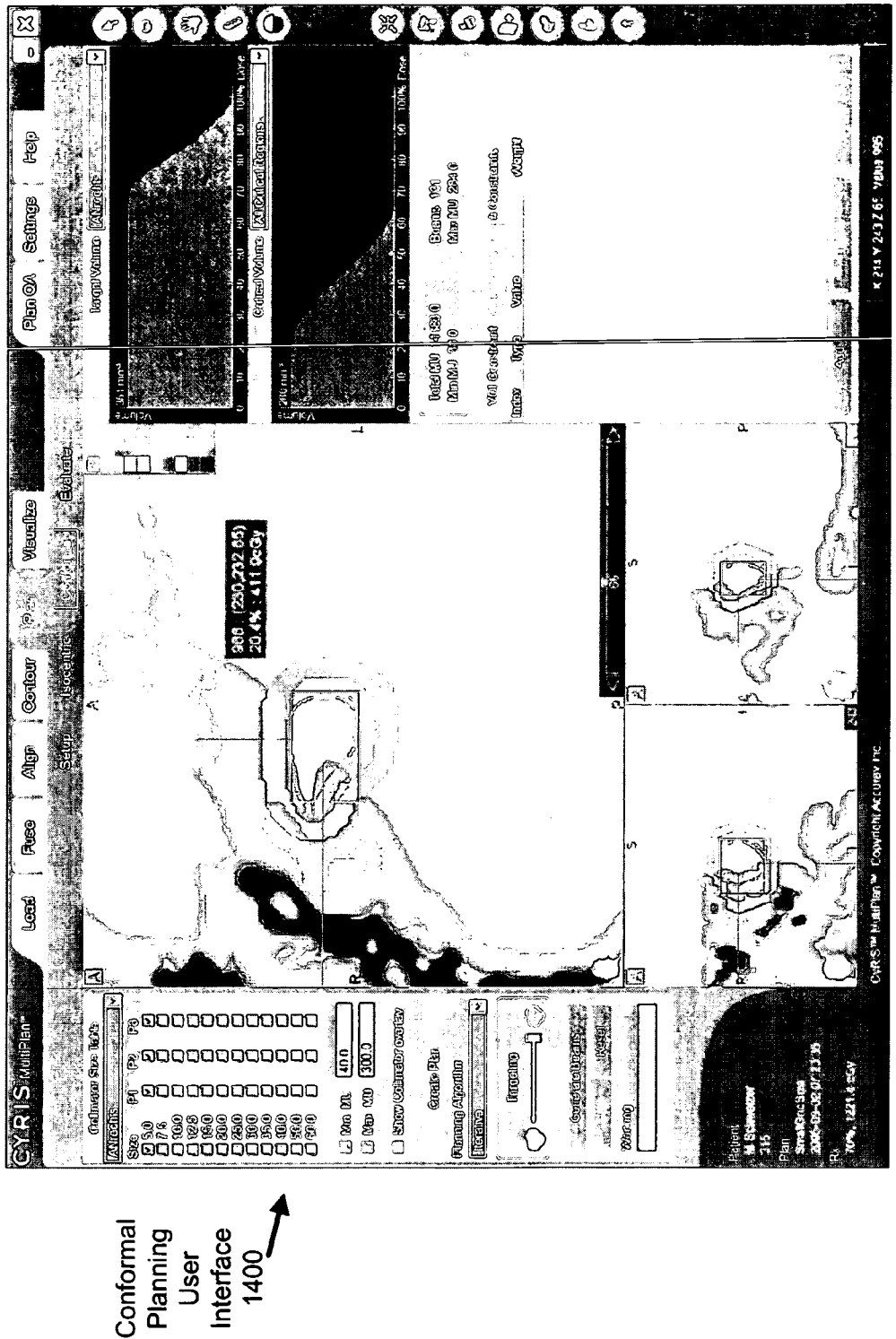
FIG. 19 illustrates one embodiment of a conformal planning user interface displaying point dose information.

In one embodiment, the conformal planning user interface 1400 may include the ability to add or delete constraint points to improve the shape of the dose isocontour. A VOI Dose Constraint Panel 1430 is provided near the right side of the display that allows the user to Add, Delete, or Delete All of the point constraints. Exemplary constraints are listed above this panel 1430. For example, after a point constraint is added, the user may then define whether that constraint point is a minimum or maximum constraint, the limit value, and the weight. A user may click on a position on the displayed image and a point constraint may appear, for example, as a small dot or cross-hair planar view. The point constraint may be displayed with its associated values (e.g., position, percentage, and dose), as illustrated by box 1910 in conformal planning user interface 1400 of FIG. 19.

Near the right side of the conformal user interface of FIG. 14 are a target volume DVH 1440 and a critical volume DVH 1450. For example, the top DVH corresponds to the target region and the bottom DVH corresponds to the right eye critical region. For example, using an iterative algorithm, with each optimization iteration, the resultant updated DVH information may be displayed in target volume DVH 1440 and a critical volume DVH 1450. Alternatively, the DVH's may be updated after a predetermined amount of time (e.g., five seconds). In another embodiment, the DVH's may be updated after each iteration, or the predetermined time, whichever is longer.

In one embodiment, the conformal planning user interface 1400 may also display beam statistics in box 1455, for example, the total MU 1460 and number of beams 1470, the minimum non-zero MU of all currently existing beams and the maximum MU. These statistics may also be continually updated by the TPS at the end of each optimization iteration.

In one embodiment, each dose isocontour for the target region may be represented by a unique color, which in turn corresponds to the percentage of the maximum dose to the entire target volume. For example, the orange isocontour represents 80% dose, which indicates that everything contained within the orange dose isocontour will receive at least 80% of the maximum dose.

Figure 16:
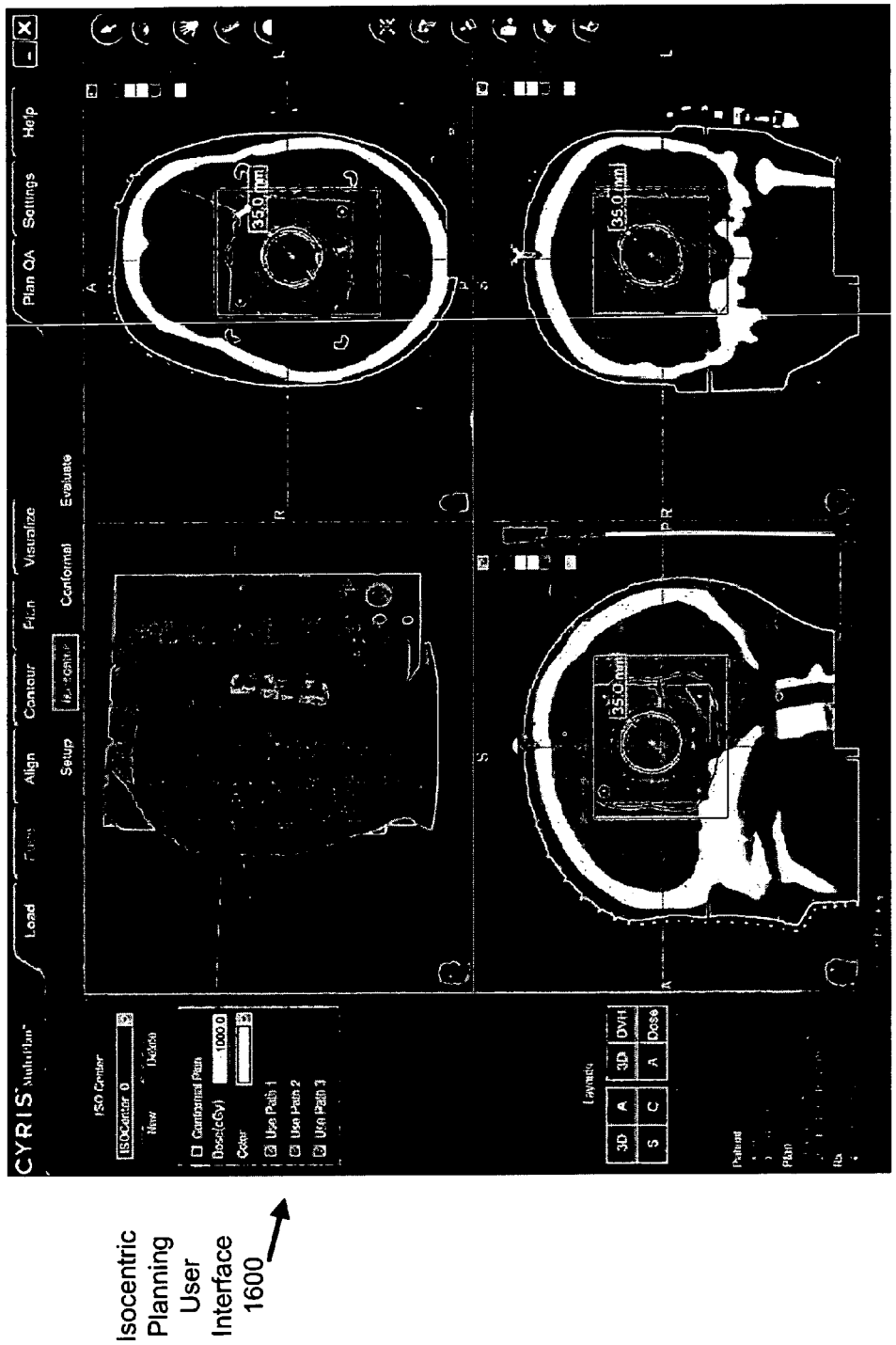
FIG. 16 illustrates one embodiment of an isocentric planning user interface.

FIG. 16 illustrates one embodiment of an isocentric planning user interface. In isocentric planning, multiple beams are directed to a single target, forming a dose sphere. The size of the sphere may depend on the collimator size, and in one embodiment, the collimator may have a diameter of about 30 millimeters as measured at about 800 millimeters from the radiation source. To treat a target pathological anatomy, multiple dose spheres are superimposed on each other in an attempt to obtain a contour that closely matches the shape of the pathological anatomy. Isocentric planning may be best applied when treating a pathological anatomy that has a substantially spherical shape.

Under the ISO Center heading near the left side of the screen, a pull-down menu provides a listing of all the current isocenters. The selected isocenters becomes active and is shown in color on the two-dimensional images, and its properties are also displayed near the left side of the screen. Isocenters may be created, resized, moved, or deleted from the user interface shown in FIG. 16. The user interface also allows for the changing of isocenters properties, such as dose (cGy), color, and path sets. In one embodiment, aspects of conformal planning may be integrated with isocentric planning. For example, by checking the Conformal box, the beam geometry (i.e., the target and collimator size of the beam set) will be created with isocentric planning, but the weights of the beams will be assigned later during conformal planning.

In one embodiment, the treatment planning process may involve aspects of both forward and inverse planning techniques, thereby combining the strengths of forward and inverse planning techniques. For example, the operator can utilize isocentric beam geometries or a mixture of non-isocentric and isocentric beam geometries as part of forward planning and subsequently modify the topology of isodose contours directly during inverse planning using aspects of the optimization process described herein (e.g., the method described with respect to flowchart 800). The operator can control each beam for use in the treatment plan in terms of radiation emission point, a distance to the target region, an orientation, and a radiation dose weight. The treatment planning software can allow the operator to specify a set of beams (and associated paths, emission points, and dose weights) to be used as part of a forward planning process, and another set of beams to be used as part of inverse planning. The set of beams reserved for inverse planning may be optimized by utilizing one or more envelope of constraint points generated automatically by the treatment planning software.

Figure 17:
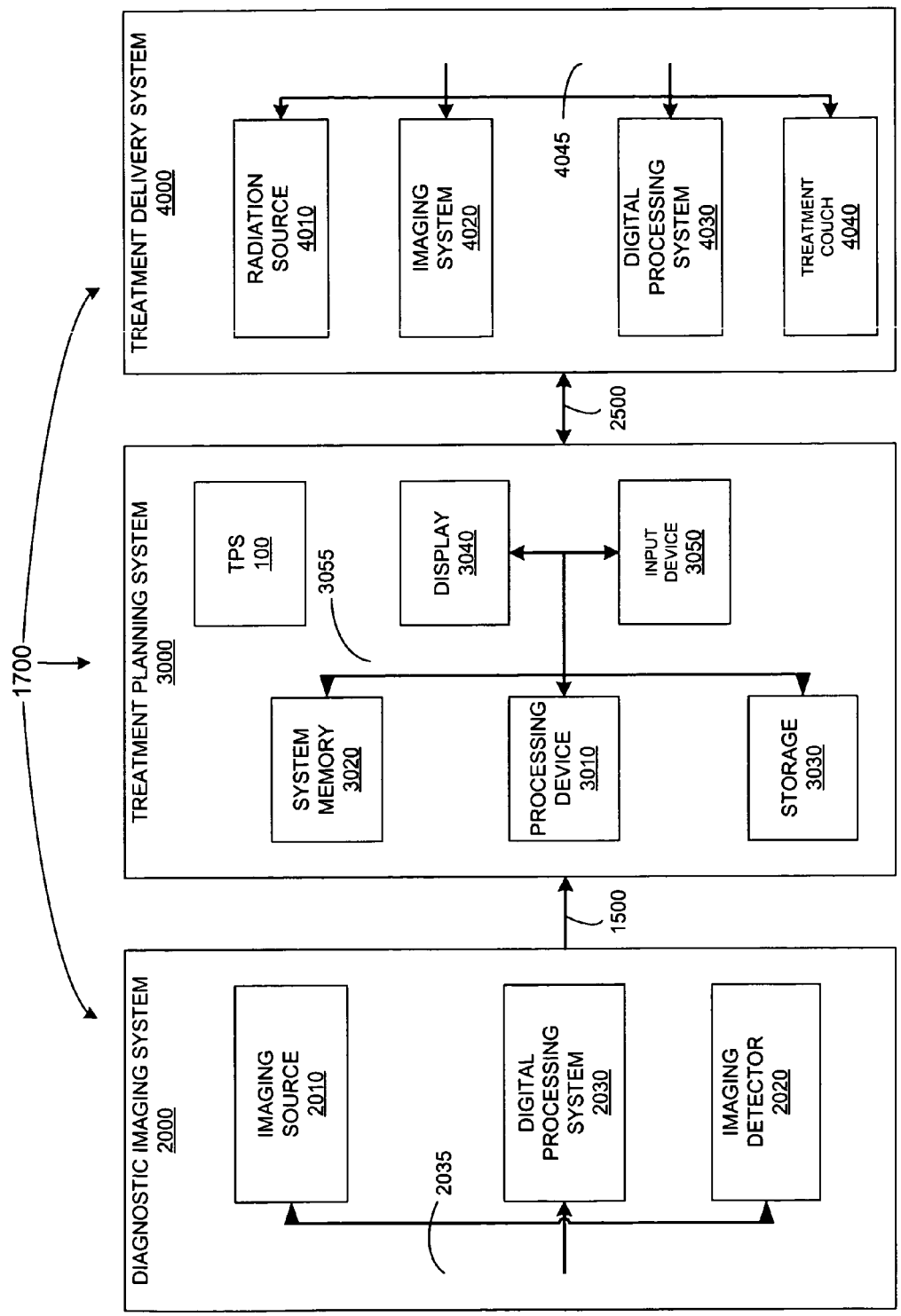
FIG. 17 illustrates one embodiment of systems that may be used to perform radiation treatment in which features of the present invention may be implemented.

FIG. 17 illustrates one embodiment of systems that may be used to perform radiation treatment in which features of the present invention may be implemented. As described below and illustrated in FIG. 17, system 1700 may include a diagnostic imaging system 2000, a treatment planning system 3000, and a treatment delivery system 4000.

Diagnostic imaging system 2000 may be any system capable of producing medical diagnostic images of a volume of interest (VOI) in a patient that may be used for subsequent medical diagnosis, treatment planning and/or treatment delivery. For example, diagnostic imaging system 2000 may be a computed tomography (CT) system, a magnetic resonance imaging (MRI) system, a positron emission tomography (PET) system, an ultrasound system or the like. For ease of discussion, diagnostic imaging system 2000 may be discussed below at times in relation to a CT x-ray imaging modality. However, other imaging modalities such as those above may also be used.

Diagnostic imaging system 2000 includes an imaging source 2010 to generate an imaging beam (e.g., x-rays, ultrasonic waves, radio frequency waves, etc.) and an imaging detector 2020 to detect and receive the beam generated by imaging source 2010, or a secondary beam or emission stimulated by the beam from the imaging source (e.g., in an MRI or PET scan). In one embodiment, diagnostic imaging system 2000 may include two or more diagnostic X-ray sources and two or more corresponding imaging detectors. For example, two x-ray sources may be disposed around a patient to be imaged, fixed at an angular separation from each other (e.g., 90 degrees, 45 degrees, etc.) and aimed through the patient toward (an) imaging detector(s) which may be diametrically opposed to the x-ray sources. A single large imaging detector, or multiple imaging detectors, may also be used that would be illuminated by each x-ray imaging source. Alternatively, other numbers and configurations of imaging sources and imaging detectors may be used.

The imaging source 2010 and the imaging detector 2020 are coupled to a digital processing system 2030 to control the imaging operation and process image data. Diagnostic imaging system 2000 includes a bus or other means 2035 for transferring data and commands among digital processing system 2030, imaging source 2010 and imaging detector 2020. Digital processing system 2030 may include one or more general-purpose processors (e.g., a microprocessor), special purpose processor such as a digital signal processor (DSP) or other type of device such as a controller or field programmable gate array (FPGA). Digital processing system 2030 may also include other components (not shown) such as memory, storage devices, network adapters and the like. Digital processing system 2030 may be configured to generate digital diagnostic images in a standard format, such as the DICOM (Digital Imaging and Communications in Medicine) format, for example. In other embodiments, digital processing system 2030 may generate other standard or non-standard digital image formats. Digital processing system 2030 may transmit diagnostic image files (e.g., the aforementioned DICOM formatted files) to treatment planning system 3000 over a data link 1500, which may be, for example, a direct link, a local area network (LAN) link or a wide area network (WAN) link such as the Internet. In addition, the information transferred between systems may either be pulled or pushed across the communication medium connecting the systems, such as in a remote diagnosis or treatment planning configuration. In remote diagnosis or treatment planning, a user may utilize embodiments of the present invention to diagnose or treatment plan despite the existence of a physical separation between the system user and the patient.

Treatment planning system 3000 includes a processing device 3010 to receive and process image data. Processing device 3010 may represent one or more general-purpose processors (e.g., a microprocessor), special purpose processor such as a digital signal processor (DSP) or other type of device such as a controller or field programmable gate array (FPGA). Processing device 3010 may be configured to execute instructions for performing the operations of the TPS 100 discussed herein that, for example, may be loaded in processing device 3010 from storage 3030 and/or system memory 3020.

Treatment planning system 3000 may also include system memory 3020 that may include a random access memory (RAM), or other dynamic storage devices, coupled to processing device 3010 by bus 3055, for storing information and instructions to be executed by processing device 3010. System memory 3020 also may be used for storing temporary variables or other intermediate information during execution of instructions by processing device 3010. System memory 3020 may also include a read only memory (ROM) and/or other static storage device coupled to bus 3055 for storing static information and instructions for processing device 3010.

Treatment planning system 3000 may also include storage device 3030, representing one or more storage devices (e.g., a magnetic disk drive or optical disk drive) coupled to bus 3055 for storing information and instructions. Storage device 3030 may be used for storing instructions for performing the treatment planning methods discussed herein.

Processing device 3010 may also be coupled to a display device 3040, such as a cathode ray tube (CRT) or liquid crystal display (LCD), for displaying information (e.g., a two-dimensional or three-dimensional representation of the VOI) to the user. An input device 3050, such as a keyboard, may be coupled to processing device 3010 for communicating information and/or command selections to processing device 3010. One or more other user input devices (e.g., a mouse, a trackball or cursor direction keys) may also be used to communicate directional information, to select commands for processing device 3010 and to control cursor movements on display 3040.

It will be appreciated that treatment planning system 3000 represents only one example of a treatment planning system, which may have many different configurations and architectures, which may include more components or fewer components than treatment planning system 3000 and which may be employed with the present invention. For example, some systems often have multiple buses, such as a peripheral bus, a dedicated cache bus, etc. The treatment planning system 3000 may also include MIRIT (Medical Image Review and Import Tool) to support DICOM import (so images can be fused and targets delineated on different systems and then imported into the treatment planning system for planning and dose calculations), expanded image fusion capabilities that allow the user to treatment plan and view dose distributions on any one of various imaging modalities (e.g., MRI, CT, PET, etc.). Treatment planning systems are known in the art; accordingly, a more detailed discussion is not provided.

Treatment planning system 3000 may share its database (e.g., data stored in storage device 3030) with a treatment delivery system, such as treatment delivery system 4000, so that it may not be necessary to export from the treatment planning system prior to treatment delivery. Treatment planning system 3000 may be linked to treatment delivery system 4000 via a data link 2500, which may be a direct link, a LAN link or a WAN link as discussed above with respect to data link 1500. It should be noted that when data links 1500 and 2500 are implemented as LAN or WAN connections, any of diagnostic imaging system 2000, treatment planning system 3000 and/or treatment delivery system 4000 may be in decentralized locations such that the systems may be physically remote from each other. Alternatively, any of diagnostic imaging system 2000, treatment planning system 3000 and/or treatment delivery system 4000 may be integrated with each other in one or more systems.

Treatment delivery system 4000 includes a therapeutic and/or surgical radiation source 4010 to administer a prescribed radiation dose to a target volume in conformance with a treatment plan. Treatment delivery system 4000 may also include an imaging system 4020 to capture intra-treatment images of a patient volume (including the target volume) for registration or correlation with the diagnostic images described above in order to position the patient with respect to the radiation source. Treatment delivery system 4000 may also include a digital processing system 4030 to control radiation source 4010, imaging system 4020, and a patient support device such as a treatment couch 4040. Digital processing system 4030 may include one or more general-purpose processors (e.g., a microprocessor), special purpose processor such as a digital signal processor (DSP) or other type of device such as a controller or field programmable gate array (FPGA). Digital processing system 4030 may also include other components (not shown) such as memory, storage devices, network adapters and the like. Digital processing system 4030 may be coupled to radiation source 4010, imaging system 4020 and treatment couch 4040 by a bus 4045 or other type of control and communication interface.

Figure 18:
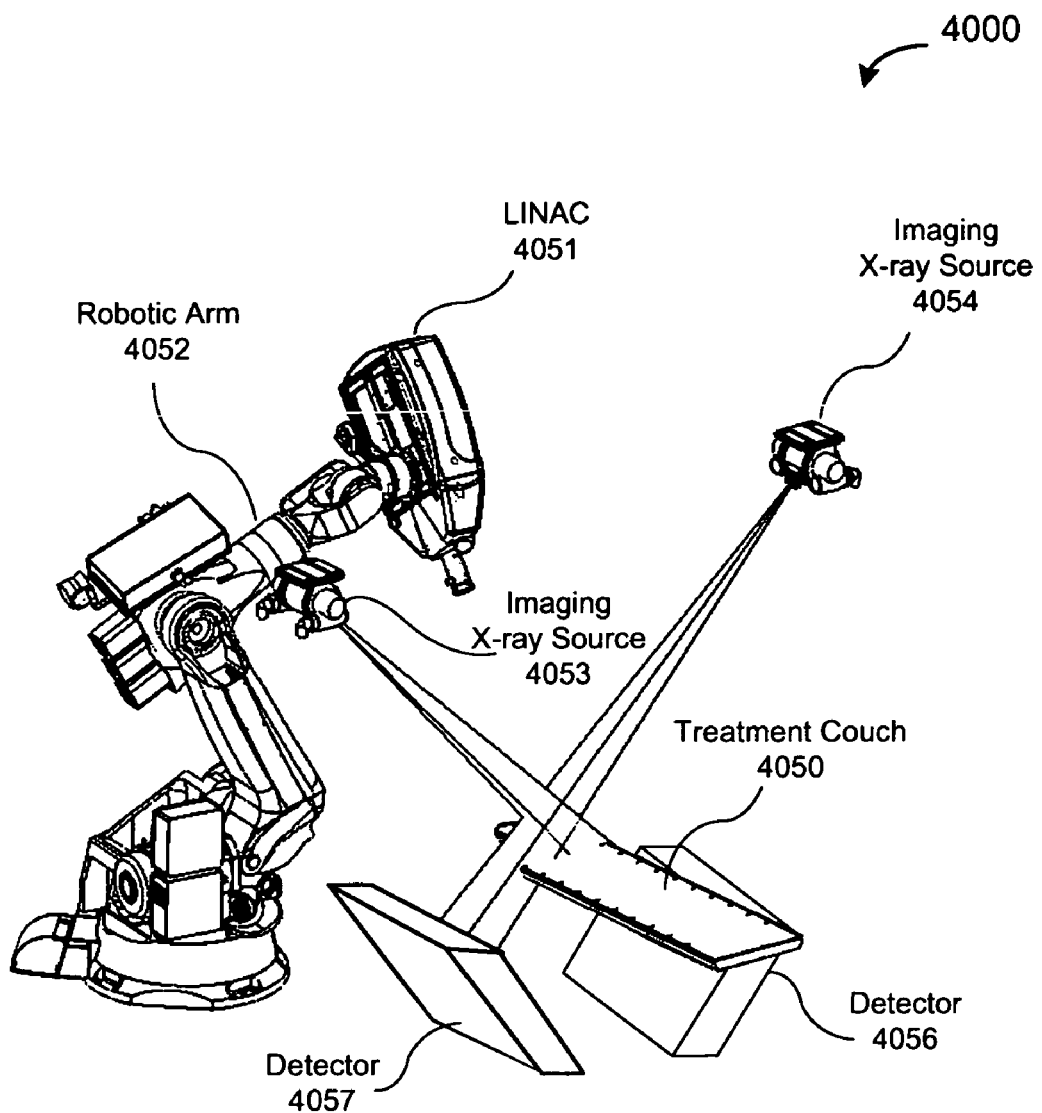
FIG. 18 illustrates one embodiment of a diagnostic imaging system, a treatment planning system and a treatment delivery system.

In one embodiment, as illustrated in FIG. 18, treatment delivery system 4000 may be an image-guided, robotic-based radiation treatment system (e.g., for performing radiosurgery) such as the CyberKnife® system developed by Accuray Incorporated of California. In FIG. 18, radiation source 4010 may be represented by a linear accelerator (LINAC) 4051 mounted on the end of a robotic arm 4052 having multiple (e.g., 5 or more) degrees of freedom in order to position the LINAC 4051 to irradiate a pathological anatomy (target region or volume) with beams delivered from many angles in an operating volume (e.g., a sphere) around the patient. Treatment may involve beam paths with a single isocenter (point of convergence), multiple isocenters, or with a non-isocentric approach (i.e., the beams need only intersect with the pathological target volume and do not necessarily converge on a single point, or isocenter, within the target as illustrated in FIG. 15). Treatment can be delivered in either a single session (mono-fraction) or in a small number of sessions as determined during treatment planning. With treatment delivery system 4000, in one embodiment, radiation beams may be delivered according to the treatment plan without fixing the patient to a rigid, external frame to register the intra-operative position of the target volume with the position of the target volume during the pre-operative treatment planning phase.

In FIG. 18, imaging system 4020 may be represented by X-ray sources 4053 and 4054 and X-ray image detectors (imagers) 4056 and 4057. In one embodiment, for example, two x-ray sources 4053 and 4054 may be nominally aligned to project imaging x-ray beams through a patient from two different angular positions (e.g., separated by 90 degrees, 45 degrees, etc.) and aimed through the patient on treatment couch 4050 toward respective detectors 4056 and 4057. In another embodiment, a single large imager can be used that would be illuminated by each x-ray imaging source. Alternatively, other numbers and configurations of imaging sources and imagers may be used.

Digital processing system 4030 may implement algorithms to register images obtained from imaging system 4020 with pre-operative treatment planning images in order to align the patient on the treatment couch 4050 within the treatment delivery system 4000, and to precisely position the radiation source with respect to the target volume.

The treatment couch 4050 may be coupled to another robotic arm (not illustrated) having multiple (e.g., 5 or more) degrees of freedom. The couch arm may have five rotational degrees of freedom and one substantially vertical, linear degree of freedom. Alternatively, the couch arm may have six rotational degrees of freedom and one substantially vertical, linear degree of freedom or at least four rotational degrees of freedom. The couch arm may be vertically mounted to a column or wall, or horizontally mounted to pedestal, floor, or ceiling. Alternatively, the treatment couch 4050 may be a component of another mechanical mechanism, such as the Axum® treatment couch developed by Accuray Incorporated of California, or be another type of conventional treatment table known to those of ordinary skill in the art.

Alternatively, treatment delivery system 4000 may be another type of treatment delivery system, for example, a gantry based (isocentric) intensity modulated radiotherapy (IMRT) system. In a gantry based system, a radiation source (e.g., a LINAC) is mounted on the gantry in such a way that it rotates in a plane corresponding to an axial slice of the patient. Radiation is then delivered from several positions on the circular plane of rotation. In IMRT, the shape of the radiation beam is defined by a multi-leaf collimator that allows portions of the beam to be blocked, so that the remaining beam incident on the patient has a pre-defined shape. The resulting system generates arbitrarily shaped radiation beams that intersect each other at the isocenter to deliver a dose distribution to the target. In IMRT planning, the optimization algorithm selects subsets of the main beam and determines the amount of time that the patient should be exposed to each subset, so that the prescribed dose constraints are best met.

In other embodiments, yet another type of treatment delivery system 4000 may be used, for example, a stereotactic frame system such as the GammaKnife®, available from Elekta of Sweden. In such a frame-based radiosurgery system, a distributed radiation source (e.g., a cobalt 60 gamma ray source) is used to produce an approximately hemispherical distribution of simultaneous radiation beams though holes in a beam-forming assembly. The axes of the radiation beams are angled to intersect at a single point (treatment isocenter) and the beams together form an approximately spherical locus of high intensity radiation. The distributed radiation source requires heavy shielding, and as a result the equipment is heavy and immobile. Therefore, the system is limited to a single treatment isocenter. In such a system, the optimization algorithm may be referred to as a sphere packing algorithm (i.e., due to the hemispherical distribution of simultaneous radiation beams though holes in a beam-forming assembly) and determines the selection and dose weighting assigned to a group of beams forming isocenters in order to best meet provided dose constraints.

Frame-based radiotherapy and radiosurgery treatment systems employ a rigid, invasive stereotactic frame to immobilize a patient during pre-treatment imaging for diagnosis and treatment planning (e.g., using a CT scan or other 3-D imaging modality, such as MRI or PET), and also during subsequent radiation treatments. These systems may be limited to intracranial treatments because the rigid frame must be attached to bony structures that have a fixed spatial relationship with target region, and the skull and brain are the only anatomical features that satisfy that criterion.

It should be noted that the methods and apparatus described herein are not limited to use only with medical diagnostic imaging and treatment. In alternative embodiments, the methods and apparatus herein may be used in applications outside of the medical technology field, such as industrial imaging and non-destructive testing of materials (e.g., motor blocks in the automotive industry, airframes in the aviation industry, welds in the construction industry and drill cores in the petroleum industry) and seismic surveying. In such applications, for example, "treatment" may refer generally to the effectuation of an operation controlled by the TPS, such as the application of a beam (e.g., radiation, acoustic, etc.).

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative sense rather than a restrictive sense.

What is claimed is:

1. A method of creating a treatment plan, comprising:
   optimizing one or more treatment planning parameters of the treatment plan with a treatment planning system to treat a target using an optimization process;
   automatically generating output of the treatment plan by the optimization process after an intermediate iteration of the optimization process, without user intervention, prior to termination of the optimization process; and
   updating treatment plan data displayed to a user of the treatment planning system based on the output generated by the intermediate iteration prior to the termination of the optimization process.

2. The method of claim 1, wherein updating the treatment plan data comprises updating data displayed to the user after one or more additional iterations of the optimization process.

3. The method of claim 1, wherein updating the treatment plan data comprises updating data displayed to the user after each of the one or more additional iterations of the optimization process.

4. The method of claim 1, wherein the optimization process comprises an iterative algorithm.

5. The method of claim 4, wherein the optimization process further comprises a simplex algorithm.

6. The method of claim 5, wherein updating the treatment plan data is performed after completion of the simplex algorithm but before running of the iterative algorithm.

7. The method of claim 1, wherein updating the treatment plan data displayed to the user comprises updating a dose volume histogram.

8. The method of claim 7, where the dose volume histogram is a target dose volume histogram.

9. The method of claim 7, where the dose volume histogram is a critical structure dose volume histogram.

10. The method of claim 1, wherein updating the treatment plan data displayed to the user comprises updating a dose isocontour.

11. The method of claim 1, wherein the pathological anatomy is treated using a plurality of beams and wherein updating the treatment plan data displayed to the user comprises updating a statistic of the plurality of beams.

12. The method of claim 11, wherein the statistic comprises a number of the plurality of beams.

13. The method of claim 11, wherein the statistic comprises a total monitor units for the plurality of beams.

14. The method of claim 11, wherein the statistic comprises a minimum non-zero monitor unit of beams of the plurality of beams.

15. The method of claim 11, wherein the statistic comprises a maximum monitor units for the plurality of beams.

16. The method of claim 1, wherein updating the treatment plan data displayed to the user comprises updating a point constraint value.

17. The method of claim 16, wherein the point constraint value is a dose.

18. The method of claim 16, wherein the point constraint value is at least one of a position and a percentage.

19. The method of claim 1, wherein the target is a pathological anatomy and wherein the one or more treatment planning parameters comprises a radiation dose delivered to the pathological anatomy.

20. A method of creating a treatment plan, comprising:
optimizing one or more treatment planning parameters of the treatment plan with a treatment planning system to treat a target using an optimization process;
automatically generating output of the treatment plan by the optimization process after an intermediate iteration of the optimization process, without user intervention, prior to termination of the optimization process; and
updating treatment plan data displayed to a user of the treatment planning system based on the output generated by the intermediate iteration prior to the termination of the optimization process, wherein the one or more treatment planning parameters comprise a radiation beam emission point of a linear accelerator.

21. The method of claim 20, wherein the one or more treatment planning parameters comprise an orientation of the linear accelerator at the radiation emission point.

22. The method of claim 1, wherein the one or more treatment planning parameters comprise a shape of a radiation beam.

23. The method of claim 1, wherein the one or more treatment planning parameters comprise a duration that a radiation beam is on.

* * * * *